US008756074B2

(12) United States Patent
Brzustowicz

(10) Patent No.: US 8,756,074 B2
(45) Date of Patent: Jun. 17, 2014

(54) SYSTEMS AND METHODS FOR PROVIDING A REAL-TIME HEALTH RISK ASSESSMENT

(75) Inventor: Michael R. Brzustowicz, San Francisco, CA (US)

(73) Assignee: Michael R. Brzustowicz, San Francisco, CA (US)

(*) Notice: Subject to any disclaimer, the term of this patent is extended or adjusted under 35 U.S.C. 154(b) by 618 days.

(21) Appl. No.: 12/950,495

(22) Filed: Nov. 19, 2010

(65) Prior Publication Data
US 2012/0130194 A1    May 24, 2012

(51) Int. Cl.
*G06Q 10/00*    (2012.01)
*G06Q 50/00*    (2012.01)
*G06Q 50/22*    (2012.01)

(52) U.S. Cl.
CPC .................................. *G06Q 50/22* (2013.01)
USPC .................................................. 705/2

(58) Field of Classification Search
CPC ...... G06Q 50/22; G06Q 50/24; G06F 19/322; G06F 19/3418
USPC .................................................. 705/2
See application file for complete search history.

(56) References Cited

U.S. PATENT DOCUMENTS

| 7,996,282 | B1* | 8/2011 | Scott et al. ................... 705/27.2 |
| 8,238,999 | B2* | 8/2012 | Haider et al. ................. 600/407 |
| 2003/0158758 | A1* | 8/2003 | Kanazawa et al. ............... 705/4 |
| 2005/0065813 | A1* | 3/2005 | Mishelevich et al. ............ 705/2 |

* cited by examiner

*Primary Examiner* — Michelle L Le
(74) *Attorney, Agent, or Firm* — Morgan, Lewis & Bockius LLP

(57) ABSTRACT

Systems and methods are provided for providing a real-time health risk assessment generated based on a plurality of health parameters entered via a plurality of health parameter controls. A health parameter entry interface includes a plurality of health parameter controls to enter values, where the values include demographic parameters, health history parameters, and family history parameters. A disease risk interface includes an alphanumeric depiction of risks of a person developing one or more health conditions based on values entered using the health parameter entry interface. A disease risk location identification interface includes a picture of a human body, where when a risk of a person developing a health condition is greater than a threshold, a graphic is displayed on the picture of the human body at a position associated with the health condition.

25 Claims, 20 Drawing Sheets

SYSTEMS AND METHODS FOR PROVIDING A REAL-TIME HEALTH RISK ASSESSMENT

TECHNICAL FIELD

The present disclosure relates generally to human health analysis and more particularly to real-time health risk assessment calculation.

BACKGROUND

Health is the general condition of a person in all aspects. It is also sometimes defined as a level of functional and/or metabolic efficiency of an organism. The World Health Organization (WHO) defines health as "a state of complete physical, mental, and social well-being and not merely the absence of disease or infirmity." Every person is concerned with personal health, as one's personal health level enables or limits one's ability to perform actions in their life. People are not only concerned about the current state of their health, but they are also interested in actions they can take to improve their health, as well as behaviors that may have a negative impact on their health. Other parties, outside of an individual, may also have an interest in an individual's health level. For example, a health or life insurance company may factor a health level of an individual into pricing a premium for a policy because a person in poor health may be at a higher risk for debilitating disease or death.

SUMMARY

In accordance with the teachings herein, systems and methods are disclosed for providing a real-time health risk assessment generated based on a plurality of health parameters entered via a plurality of health parameter controls. The systems and methods may include a health parameter entry interface, where the health parameter entry interface includes the plurality of health parameter controls for manipulation by a user to enter values for the plurality of health parameters, where the plurality of health parameters include one or more demographic parameters, one or more health history parameters, and one or more family history parameters. The systems and methods may further include a disease risk interface, where the disease risk interface includes an alphanumeric depiction of risks of a person developing one or more health conditions based on the values entered for the plurality of health parameters using the health parameter entry interface. The systems and methods may further include a disease risk location identification interface, where the disease risk location identification interface includes a picture of all or a portion of a human body wherein, for each respective health condition in said one or more health conditions, a graphic is displayed on the picture of said all or said portion of the human body at a position of the human body associated with the respective health condition when a risk of a person developing the respective health condition is greater than a display threshold associated with the respective health condition. The health parameter entry interface, the disease risk interface, and the disease risk location identification interface may be simultaneously displayed on a computer display, and the alphanumeric depiction of risks of a person developing one or more health conditions and the display of graphics on the picture of said all or said portion of the human body may be updated substantially simultaneously with changes to the plurality of health parameters in the health parameter entry interface.

The details of one or more embodiments of the invention are set forth in the accompanying drawings and the description below. Other features, aspects, and advantages of the invention will become apparent from the description, the drawings, and the claims.

DETAILED DESCRIPTION

Figure 1:
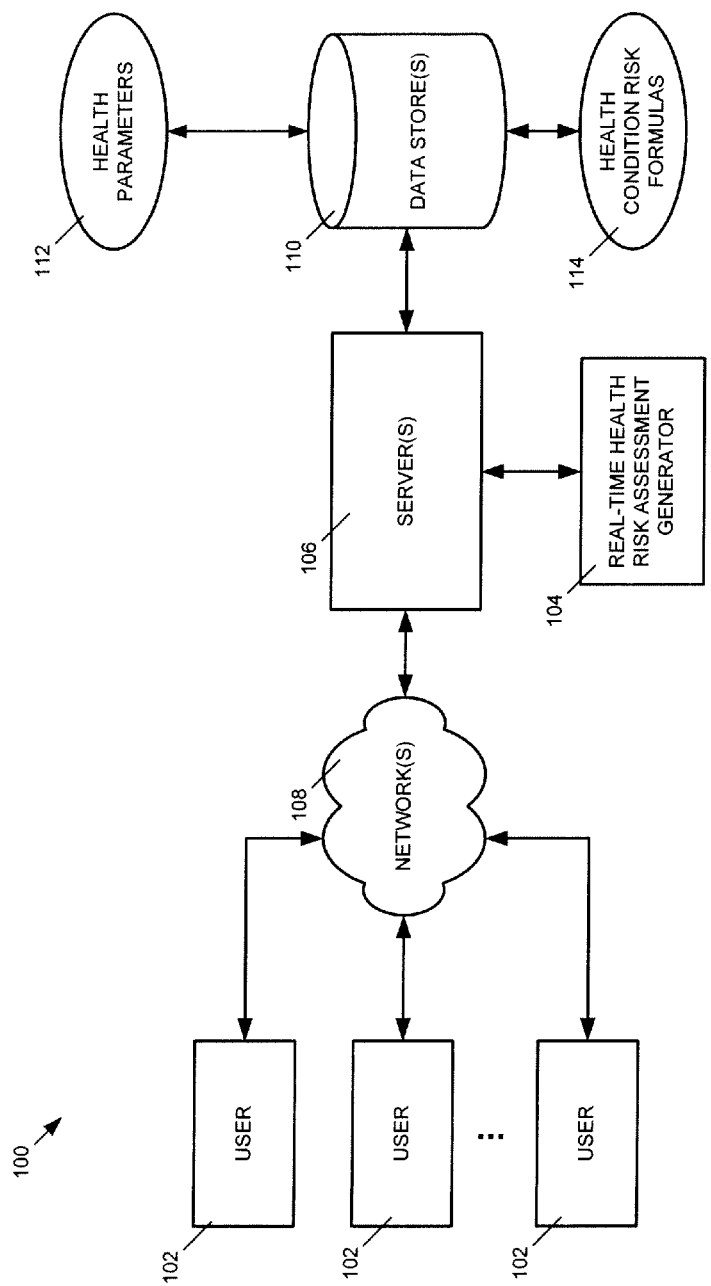
FIG. 1 depicts a computer-implemented environment for providing a real-time health risk assessment.

FIG. 1 depicts a computer-implemented environment for providing a real-time health risk assessment. A user 102 interacts with a real-time health risk assessment generator 104 on one or more servers 106 via one or more networks 108. The user may interact with the real-time health risk assessment generator 104 to perform a variety of functions, such as performing a self-real-time health risk assessment or performing a real-time health risk assessment for another individual, such as for generating a health or life insurance premium quotation, or performing a health risk assessment to recommend treatment in a doctor's office or other clinical setting.

Oftentimes, people are concerned with their overall health and their risks for developing certain debilitating conditions over time. While, data about one's risks is highly desirable, it can be very expensive to acquire. For example, hiring a medical doctor to perform an analysis of one's current health may include significant physical examinations along with substantial inquiry into personal and family histories. Each of these may be very expensive and are often highly invasive. These factors make such inquiries into personal health and risk factors unfeasible for many individuals.

Analysis of an individual's health and risks of developing debilitating conditions may also be valuable to entities other than the individual. For example, an insurance company or employer may desire knowledge of an individual's health and wellbeing for determinations regarding insurance underwriting, hiring, and other decisions. The expense of such analyses by a doctor may make such full health workups impractical when the cost of such procedures is greater than the potential savings such additional health data may make available.

The real-time health risk assessment generator 104 makes data concerning current health and future risks of developing certain conditions readily available for an individual as well as other parties having an interest in the health of an individual. Certain parameters, most of which are readily available/accessible, are entered into the real-time health risk assessment generator 104 for an individual. The real-time health risk assessment generator 104 analyzes the entered data and provides an analysis of the individual's risks for developing certain conditions. The real-time health risk assessment generator 104 may also provide suggested behaviors for improving an individual's health and reducing risks of generating the certain conditions, as well as provide updated risk data that the individual could expect should the individual implement the real-time health risk assessment generator's suggested behaviors. The real-time health risk assessment generator 104 may track parameters entered for an individual over time to detect improvement or decline in overall health and the affect of the improving/declining health on the risks for developing the certain conditions.

The users 102 can interact with the real-time health risk assessment generator 104 in a number of ways, such as over one or more networks 108. For example, server(s) 106 accessible through the network(s) 108 can host the real-time health risk assessment generator 104. One or more data stores 110 can store data used by the real-time health risk assessment generator 104 as well as any intermediate or final data generated by the real-time health risk assessment generator 104. The one or more data stores 110 may contain many different types of data associated with the process including entered health parameter values 112, health condition risk formulas 114, as well as other data. The real-time health risk assessment generator 104 can be an integrated web-based reporting and analysis tool that provides users flexibility and functionality for providing a real-time health risk assessment. It should be understood that the real-time health risk assessment generator 104 could also be provided on a stand-alone computer. It should also be understood that the real-time health risk assessment generator 104 may be utilized with hardware implementations of software such as field-programmable gate arrays.

Figure 2:
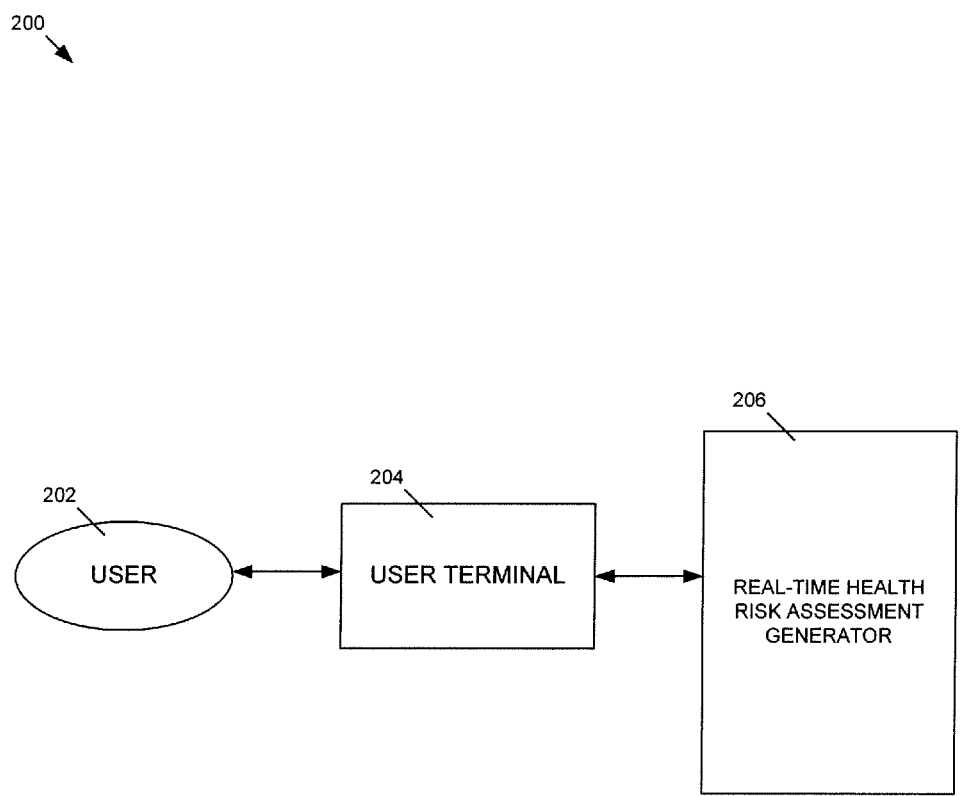
FIG. 2 is a block diagram depicting a user interacting with a user terminal to access a real-time health risk assessment generator.

FIG. 2 is a block diagram depicting a user 202 interacting with a user terminal 204 to access a real-time health risk assessment generator 206. As described above, the user 202 may be an individual desiring a self-assessment of his current health and risk levels or the user 202 may be another party interested in the health and risk levels of an individual for which data is entered into the real-time health assessment generator via the user terminal 204. The real-time health risk assessment generator 206 enables very fast generation of real-time health risk assessments such that those assessments can be provided on a regular basis (e.g., hourly, daily, weekly, monthly, yearly), as desired by the user.

Figure 3:
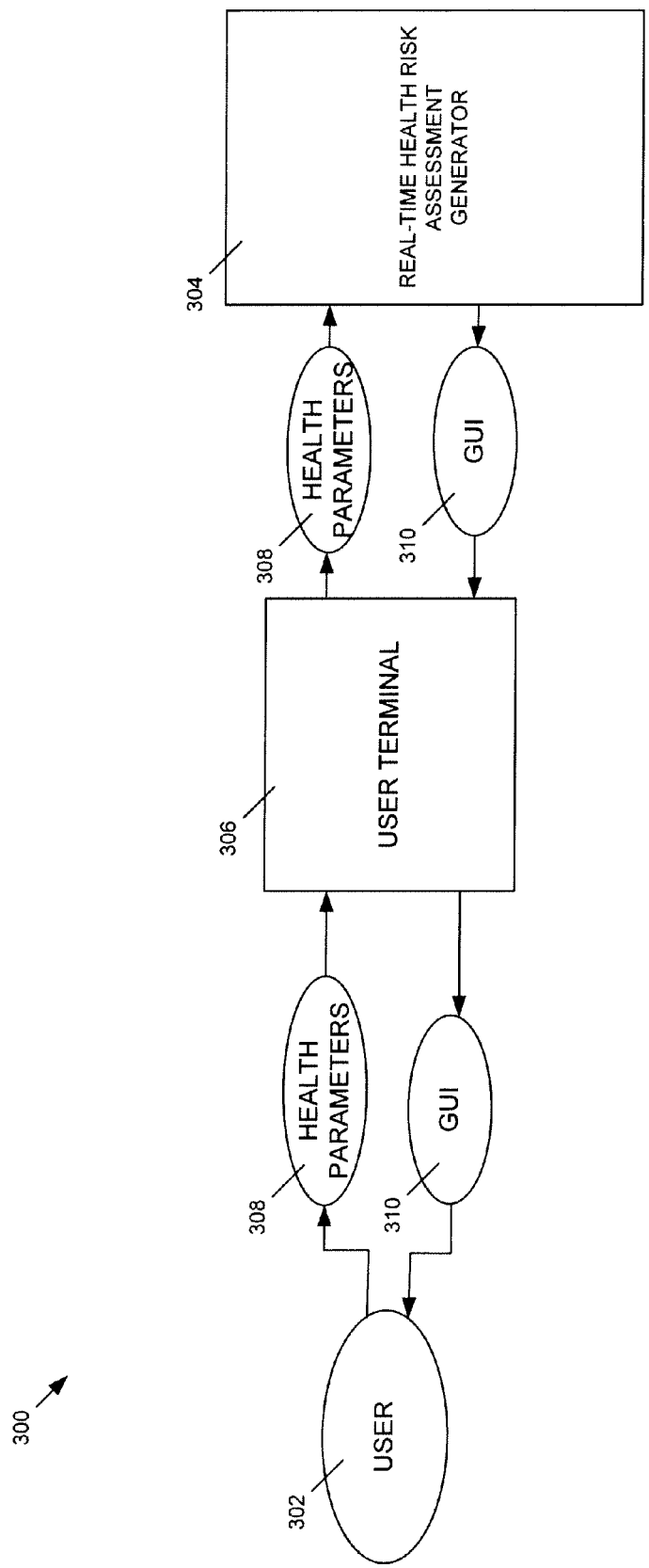
FIG. 3 is a block diagram further depicting a user interacting with a real-time health risk assessment generator via a user terminal.

FIG. 3 is a block diagram further depicting a user 302 interacting with a real-time health risk assessment generator 304 via a user terminal 306. The user 302 enters values for a plurality of health parameters 308 associated with an individual into the user terminal 306, which provides the values for the plurality of health parameters 308 to the real-time health risk assessment generator 304. The real-time health risk assessment generator 304 analyzes the received values for the health parameters 308 and calculates risk values for the individual developing certain health conditions. The real-time health risk assessment generator 310 provides a graphical user interface (GUI) 310 to the user terminal 306, which displays the graphical user interface 310 to the user 302. The graphical user interface 310 may contain a variety of data including confirmation of the health parameter values 308 entered by the user, the risks of the individual associated with the health parameter values 308 of developing certain conditions, as well as one or more graphics that depict locations of a body associated with conditions for which the individual has greater than a threshold risk of acquiring.

Figure 4:
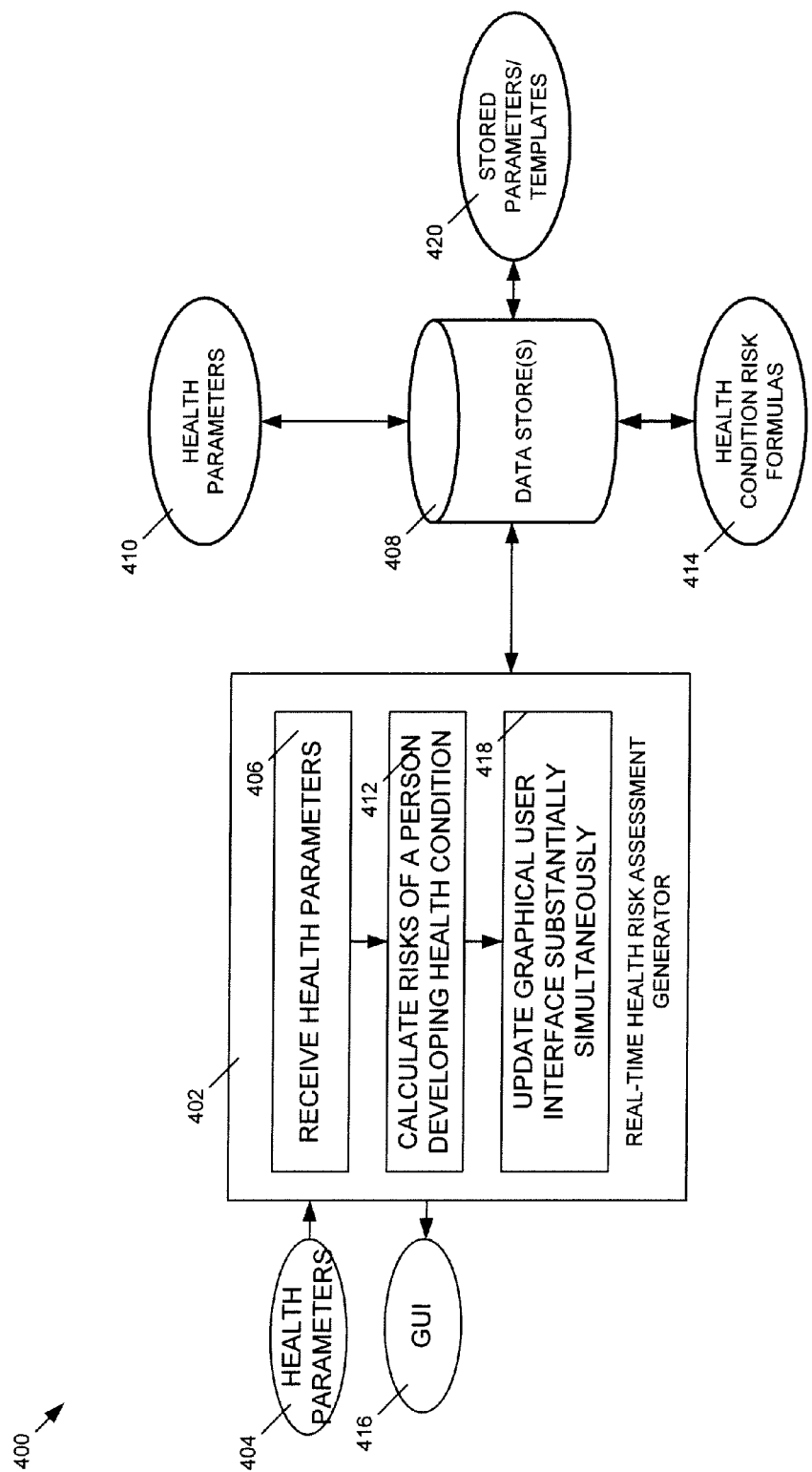
FIG. 4 is a block diagram depicting example inputs and outputs to a real-time health risk assessment generator.

FIG. 4 is a block diagram depicting example inputs and outputs to a real-time health risk assessment generator 402. The real-time health risk assessment generator 402 receives values for health parameters 404 for an individual, as depicted at 406. The real-time health risk assessment generator 402 may store those values in one or more data store(s) 408 to which the real-time health risk assessment generator 402 is responsive, as depicted at 410. The real-time health risk assessment generator 402 calculates risks of an individual developing one or more certain health conditions, as shown at 412. For example, the real-time health risk assessment generator 402 may input values for health parameters for an individual, entered at 404 or retrieved from 410, into one or more health condition risk formulas 414 to calculate risks that an individual might acquire certain health conditions. The real-time health risk assessment generator 402 outputs a graphical user interface 416 that may display a variety of data including confirmation of entered values for health parameters 404, 410 considered in calculating risk levels for acquiring certain conditions, as well as the calculated risk levels. The real-time health risk assessment generator 402 may calculate the risk levels at 412 and update the graphical user interface 416 to display the calculated risk values substantially simultaneously with the entry of the health parameter values 404 (e.g., within less than a second, within one second, within ten seconds, without subsequent user control such as activation of a "submit" button), as depicted at 418. The one or more data stores 408 responsive to the real-time health risk assessment generator 402 may also include stored health parameter values and/or templates that may be accessible for populating the health parameter values upon user request, as shown at 420.

Figure 5:
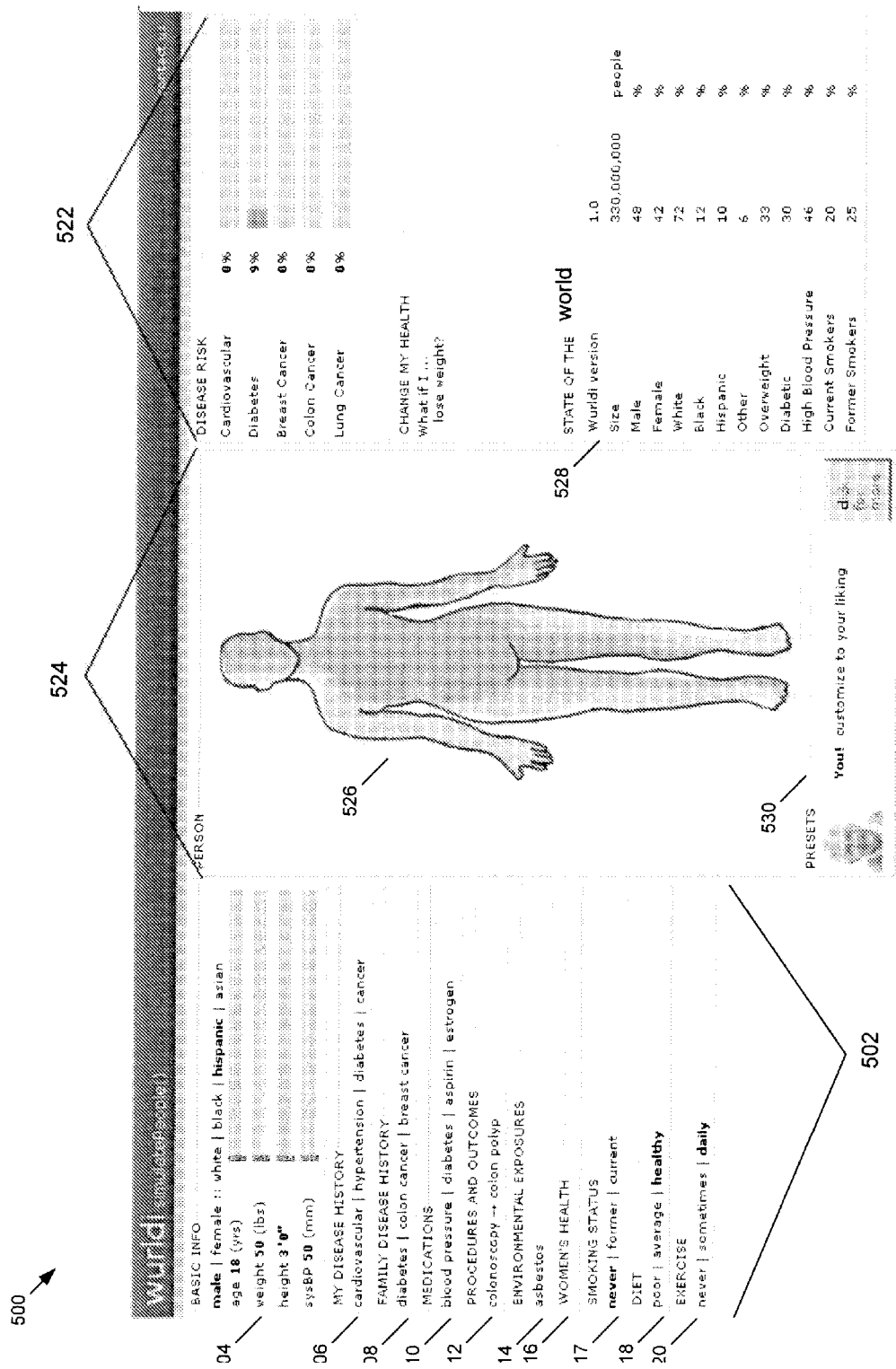
FIG. 5 depicts a graphical user interface for providing a real-time health risk assessment.

FIG. 5 depicts a graphical user interface 500 for providing a real-time health risk assessment. The graphical user interface 500 includes a health parameter entry interface 502 contained substantially in the left third of the graphical user interface 500 (e.g., within 10% of 33% of the width of the graphical user interface). The health parameter entry interface 502 includes a plurality of health parameter controls for manipulation (e.g., by a user) to enter values for a plurality of health parameters. For example, the plurality of health parameters may include one or more demographic parameters, one or more health history parameters, and one or more family history parameters.

The example health parameter entry interface 502 of FIG. 5 includes a plurality of controls for entering certain demographic and current health parameters at 504. Selectable text enables entry of whether an individual is male or female as well as entering race data. Slide bars are provided for entering data related to age, weight, height, and systolic blood pressure.

The example health parameter entry interface 502 of FIG. 5 further includes a plurality of controls for entering values for certain health history parameters. At 506, selectable text is available for selecting whether an individual has a personal history of cardiovascular disease, hypertension, diabetes, and cancer. The health parameter entry interface 502 further includes a plurality of controls for entering values for certain family disease history parameters at 508. Selectable text is provided at 508 for inputting whether family members of the individual have a history of diabetes, colon cancer, and breast cancer.

The health parameter entry interface 502 may include additional controls for inputting further data associated with an individual. For example, a medications section 510 may include controls for identifying certain medications that an individual is noted as taking. A procedures and outcomes section 512 may include controls identifying whether certain procedures have been performed on an individual and the results of those procedures. An environmental exposures section 514 may include controls for identifying whether an individual has been exposed to certain environmental factors, such as the carcinogen asbestos. A women's health section 516 may display controls specific to women's health. In some implementations, the women's health section 516 may only be made active when the individual is identified as being female in the demographic parameter entry section 504, as discussed in further detail with respect to FIG. 11. When the individual is noted as being a male, the women's health section 516 may be made inactive, as shown in FIG. 5.

The health parameter entry interface 502 may further include controls for entering data regarding a smoking history for the individual at 517. The health parameter entry interface 502 may further include controls for entering data regarding an individual's diet at 518 and an individual's exercise habits at 520.

The graphical user interface 500 may further include a disease risk interface at 522. The disease risk interface 522 may include an alphanumeric depiction of risks of an individual developing one or more health conditions based on values entered for the plurality of health parameters using the health parameter entry interface 502. The disease risk interface 522 may be displayed substantially in the right third of the graphical user interface 500 (e.g., within 10% of 33% of the width of the graphical user interface). The disease risk interface may be updated substantially simultaneously to each change at the health parameter entry interface 502, such as upon a manipulation of a slide bar in the demographic parameter entry section 504.

The graphical user interface 500 may further include a disease risk location identification interface 524. The disease risk location identification interface 524 may include a picture of all or a portion of a human body 526. For each health condition described in the disease risk interface 522, a graphic may be displayed on the picture of the human body 526 at a position of the human body associated with the health condition when a risk of the individual developing the respective health condition is greater than a display threshold value. For example, when an individual's cardio vascular disease risk is greater than 40%, then a graphic of a heart may be depicted on the picture of the human body 526. The disease risk location identification interface 524 may be displayed substantially in the center third of the graphical user interface 500 (e.g., within 10% of 33% of the width of the graphical user interface). The disease risk location identification interface may be updated substantially simultaneously to each change at the health parameter entry interface 502, such as upon a manipulation of a slide bar in the demographic parameter entry section 504.

The graphical user interface 500 may include other interfaces as well. In the example of FIG. 5, the graphical user interface includes a state of the world interface 528, where compiled values for all people or compiled values for all people who have interacted with the real-time health risk assessment generator are displayed. The graphical user interface 500 may further include a save/load profile/template interface 530. That interface 530 may enable saving or loading a template that contains values for each of the health parameters, which can be loaded into health parameter entry interface upon selection. The interface 530 may further be used to save values for each of the health parameters for an individual so that those values can be recalled at a later time.

It should be understood that the health parameter controls for entering values for health parameters may take a variety of forms. For example, health parameters 504 can be entered via selectable text and slide bars, as shown at 504. In other implementations, other controls may be utilized including text boxes, radio buttons, drop down boxes, selection boxes, and other controls. Further, the health parameter controls may include more or less controls than are depicted in FIG. 5. For example, the personal health history controls at 506 could include fewer controls or a number of additional controls related to diseases including different types of cancers, immune system disorders, endocrine disorders, as well as others.

Figure 6:
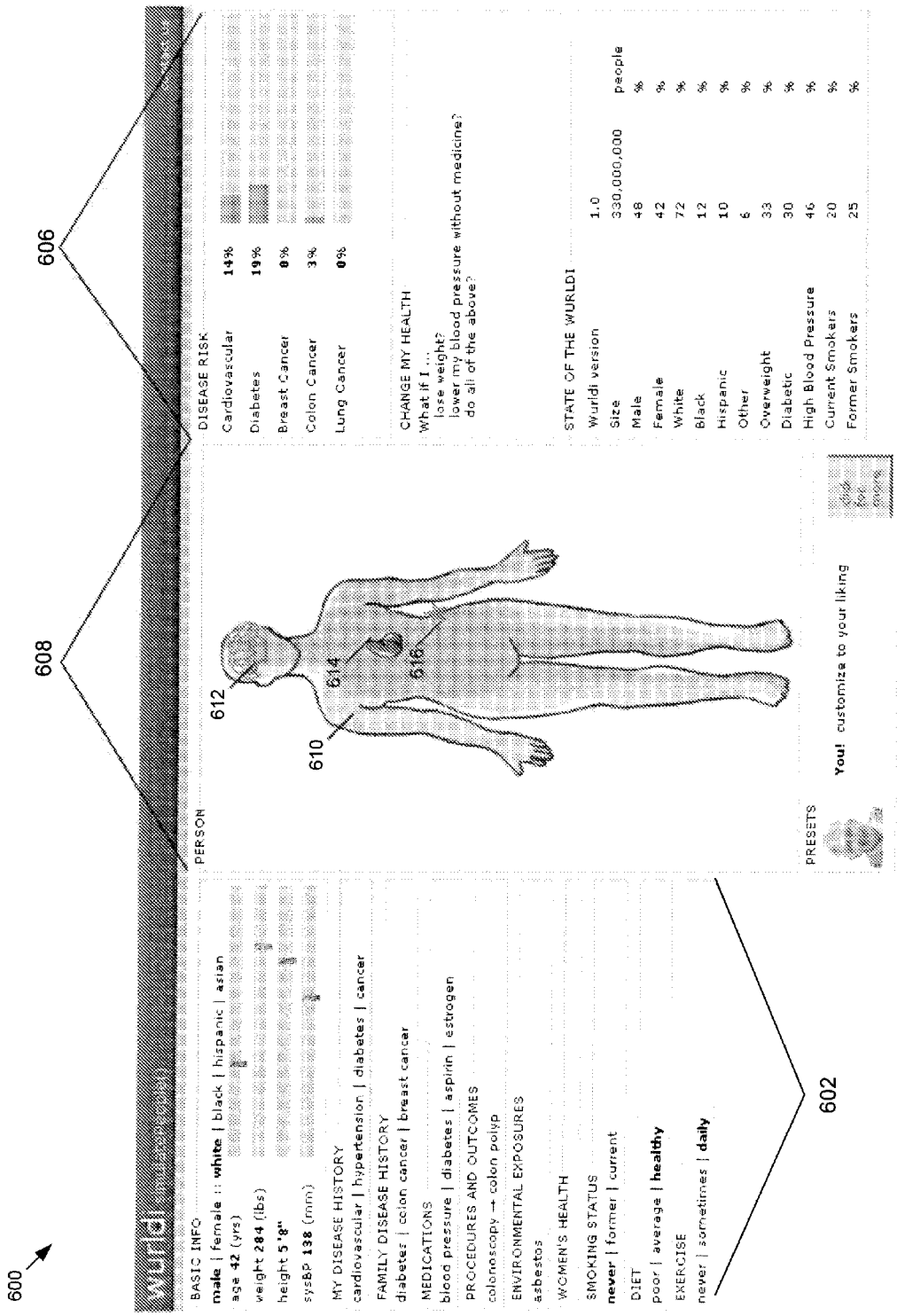
FIG. 6 depicts a graphical user interface having certain values entered into the health parameter entry interface.

FIG. 6 depicts a graphical user interface 600 having certain values entered into the health parameter entry interface 602. In the example of FIG. 6, the individual is noted as being a white male, aged 42, 5 feet, 8 inches tall, weighting 284 pounds, and having a systolic blood pressure of 138. The individual has never smoked, has a healthy diet, and exercises regularly.

The disease risk interface 606 includes an alphanumeric depiction or risks of the individual developing one or more health conditions based on the values entered in the health parameter entry interface 604. In the example of FIG. 6, the individual has a 14% risk for developing cardiovascular disease (e.g., heart attack, stroke), a 19% risk for developing diabetes, a 0% risk for developing breast cancer, a 3% risk for developing colon cancer, and a 0% risk of developing lung cancer.

The above described risks may be calculated in a variety of ways. For example, the risk for general cardiovascular disease within ten years is calculated from a logistic regression on the variables $x_i$, resulting in determination of coefficients $k_i$. The risk can then be expressed via Cox proportional hazard as $$1 - S_0^{e^{k_0 + \Sigma k_i * x_i}},$$

where, for men, $S_0=0.88431$, $k_0=-23.9802$, and the $k_i*x_i$ pairs are: 2.72107*log(age); 2.81291*log(bmi); 2.81291*log(sbp_untreated); 2.88267*log(sbp_treated); 0.61868*smoking; and 0.77763*diabetes. For women, the parameters are: $S_0=0.94833$, $k_0=-26.1931$, and the $k_i*x_i$ pairs are: 3.11296*log(age); 0.79277*log(bmi); 1.85508*log(sbp_untreated); 1.922672*log(sbp_treated); 0.70953*smoking; and 0.53160*diabetes. The treated and untreated modifiers on the blood pressure variables refer to a blood pressure medication health parameter, where if a person is identified as taking blood pressure medication, then the sbp_treated term is used, and if the person is identified as not taking blood pressure medication, then the sbp_untreated term is used.

As another example, the risk of an individual developing diabetes within ten years can be calculated from a logistic regression expressed as:

$$\frac{1}{1+e^{-(-3.02+0.19*age\_bin+0.46*is\_male+0.42*hypertension\_med+0.51*obesity)}},$$

where age_bin=1 (55≤age<60), age_bin=2 (60≤age<65), age_bin=3 (65≤age<70), age_bin=4 (70≤age<75), and obesity=1 when bmi≥30

As a further example, the risk of an individual having a breast cancer diagnosis within ten years may be calculated according to a regression expressed as $$\frac{1}{1+e^{-(var)}},$$

where var=−0.74948+0.09401*age_menopause+0.52926*number_breast_biopsies+0.21863*age_first_live_birth+0.95830*num_relatives_with_breast_cancer+0.01081*age_bin−0.28804*number_breast_biopsies*age_bin−0.19081*age_first_live_birth* num_relatives_with_breast_cancer, where age_bin=for age<50 and age_bin=1 for age≥50.

As an additional example, the risk of an individual being diagnosed with lung cancer in the next year can be calculated according to $F(1)=1-S_0^{e^{model}}$, where $S_0=0.99629$, CPD=cigarettes per day, SMK=duration of smoking, QUIT=duration of quitting, ASB=asbestos exposure, and model=−9.7960571+(0.060818386*CPD)−(0.00014652216*(CPD−15)³) for all values CPD>15+(0.00018486938*(CPD−20.185718)³) for all values CPD>20−(0.000038347226*(CPD−40)³) for all values CPD>40 +(0.11425297*SMK)−(0.000080091477*(SMK−27.6577)³) for all values SMK>27 +(0.00017069483*(SMK−40)³) for all values SMK>40−(0.000090603358*(SMK−50.910335)³) for all values SMK>50−(0.085684793*QUIT)+[0.0065499693*QUIT)³] for all values−[0.0068305845*(QUIT−0.50513347)³] for all values QUIT>0+[0.00028061519*(QUIT−12.295688)³] for all values QUIT>12+(0.070322812*AGE)−(0.00009382122*(AGE−53.459001)³) for all values AGE>53+(0.00018282661*(AGE−61.954825)³) for all values AGE>61−(0.000089005389*(AGE−70.910335)³) for all values AGE>70 +(0.2153936) if ASB=yes −(0.05827261) if SEX=female.

The ten year probability can be calculated according to $$F(10)=1-\pi(1=F(1)).$$

Further, the risk of an individual developing colon cancer within ten years can be calculated from a logistic expression expressed as $$\frac{1}{1+e^{-(z)}},$$

where for men, z=−10.549532+0.087296*age−0.704948*hasColonoscopy+0.458835*hasColonPolyp+0.728315*familyColonCancer+0.065647*exerciseHoursPerWeek−1.353137*takesAspirin−0.033220*cigarettesPerDay−0.053865*vegetablesPerDay+0.074451*bmi. For women, z=−0.661563+0.077854*age−1.031067*hasColonoscopy+0.962106*hasColonPolyp−0.109171*familyColonCancer−0.092106*exerciseHoursPerWeek−2.683215*takesAspirin+0.182743*vegetablesPerDay−0.220073*bmi−0.933628*takesEstrogen.

The risks may be calculated in a variety of ways and may represent a variety of quantities. For example, a risk level may be representative of a likelihood that an individual will develop a condition during a particular period of time such as a month, a year, five years, ten years, twenty years, a lifetime, or another period.

The disease risk location identification interface 608 may provide, for each respective health condition discussed in the disease risk interface 606, a graphic on a picture of a human body 610 at a position associated with the respective health condition when a risk of the individual developing the respective health condition is greater than a display threshold associated with the respective health condition. In the example of FIG. 6, three graphics are displayed identifying health conditions having a risk greater than the display threshold. A graphic is displayed at the brain 612 and the heart 614 based on the risk of the individual developing cardiovascular disease being at 14%. The display threshold for displaying a stroke graphic 612 may be the same or different than the display threshold for displaying a heart attack graphic 614. For example, a heart attack graphic 614 may be displayed when the cardiovascular risk is greater than 10%, while the stroke graphic 612 may be displayed with the cardiovascular risk is greater than 12%. A diabetes graphic 616 is also displayed based on the risk of the individual developing diabetes being greater than the display threshold for diabetes.

Figure 7:
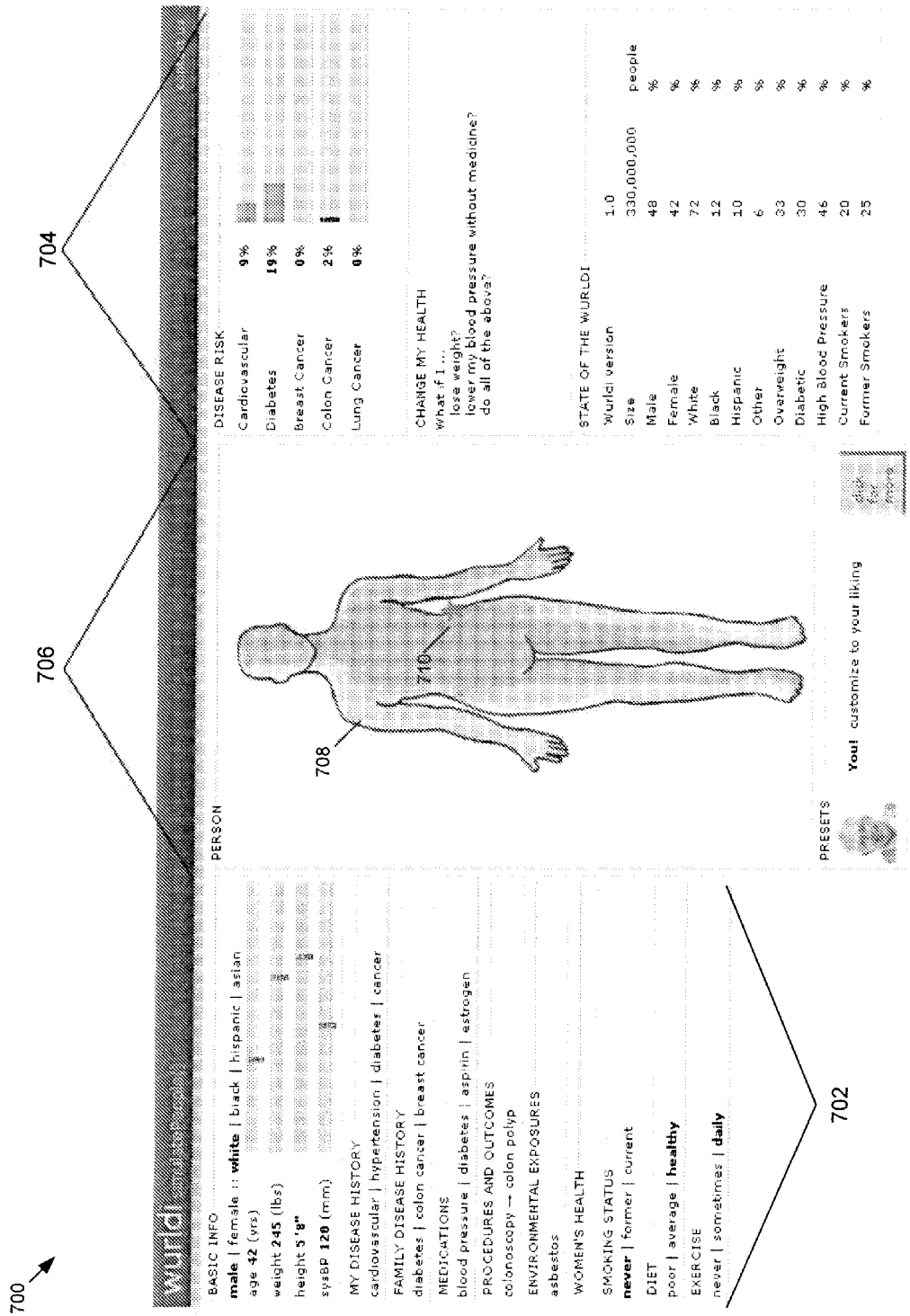
FIG. 7 depicts a graphical user interface showing reduced risks for certain health conditions based on improvement of values for certain health parameters.

FIG. 7 depicts a graphical user interface 700 showing reduced risks for certain health conditions based on improvement of values for certain health parameters. FIG. 7 depicts similar values for most of the health parameters in the health parameter entry interface 702 for the individual. In the example of FIG. 7, the individual has been noted as losing weight, down to 245 pounds, and reducing blood pressure, down to 120 systolic. The effect of the lost weight is noted in the disease risk interface 704, where the individual's risk of developing cardiovascular disease has been reduced to 9%. The reduced risk for cardiovascular disease is also noted in the disease risk location interface 706. The disease risk location interface 706 no longer depicts graphics associated with stroke and heart attack on the depiction of all or a portion of the human body 708 because the individual's risk of cardiovascular disease is lower than the display thresholds for those health conditions. The disease risk location interface 706 does depict a graphic related to diabetes 710 based on the individuals remaining at an elevated risk level for developing diabetes of 19%.

Figure 8:
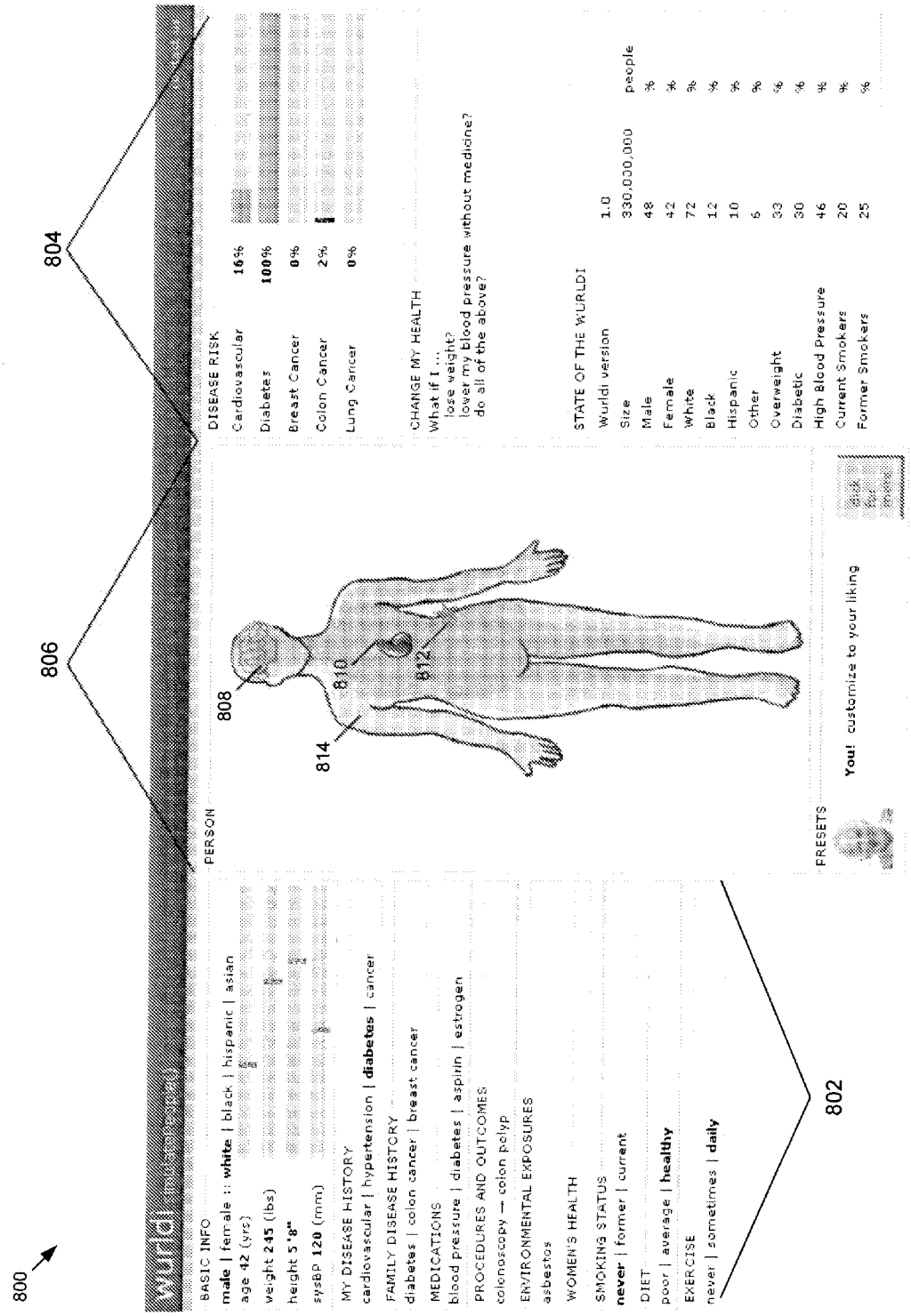
FIG. 8 depicts a graphical user interface having certain values entered into the health parameter entry interface, including a personal history of diabetes.

FIG. 8 depicts a graphical user interface 800 having certain values entered into the health parameter entry interface 802, including a personal history of diabetes. In the example of FIG. 8, the individual is noted as being a white male, aged 42, 5 feet, 8 inches tall, weighting 245 pounds, having a systolic blood pressure of 120. The individual is further noted as having a personal history of diabetes. The individual has never smoked, has a healthy diet, and exercises regularly.

The disease risk interface 804 depicts an alphanumeric representation of the risks of the individual developing certain health conditions based on the values entered in the health parameter entry interface 802. Because the individual is noted as having a personal history of diabetes, the risk of diabetes is noted as 100%. The individual also has a higher risk of cardiovascular disease, 16%, than the individual depicted in FIG. 7 having similar values for other health parameters, based on the individual in FIG. 8 having a personal history of diabetes. The disease risk location identification interface 806 includes graphics for stroke 808, heart attack 810, and diabetes 812 on the picture of the human body 814 based on the individual's elevated risks of developing those conditions.

Figure 9:
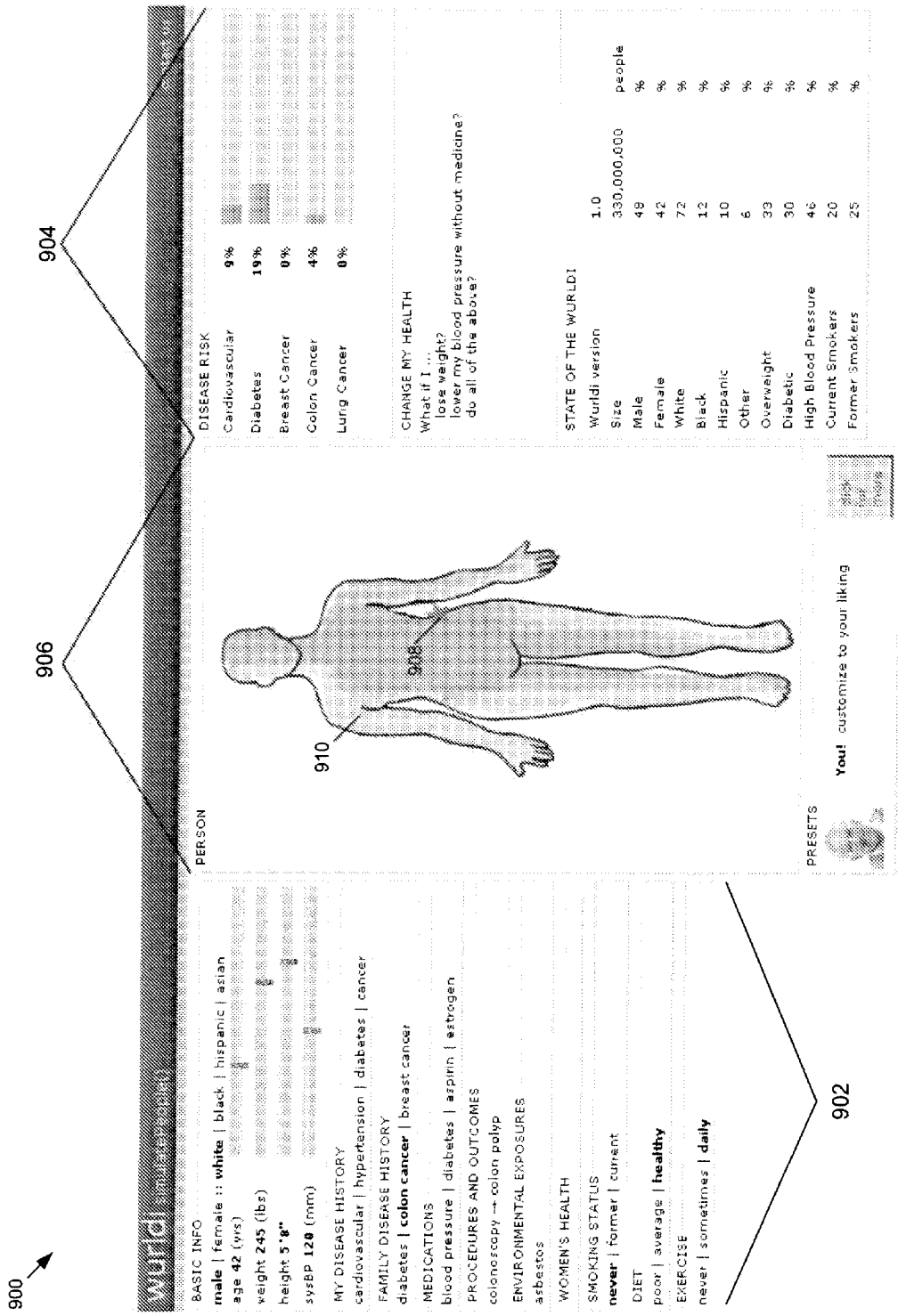
FIG. 9 depicts a graphical user interface having certain values entered into the health parameter entry interface, including a family history of colon cancer.

FIG. 9 depicts a graphical user interface 900 having certain values entered into the health parameter entry interface 902, including a family history of colon cancer. In the example of FIG. 9, the individual is noted as being a white male, aged 42, 5 feet, 8 inches tall, weighting 245 pounds, having a systolic blood pressure of 120. The individual is further noted as having a family history of colon cancer. The individual has never smoked, has a healthy diet, and exercises regularly.

The disease risk interface 904 depicts an alphanumeric representation of the risks of the individual developing certain health conditions based on the values entered in the health parameter entry interface 902. Because the individual is noted as having a family history of colon cancer, the individual's colon cancer risk is doubled to 4% over the individual depicted in FIG. 7 having similar values for several health parameters. The disease risk location identification interface 906 displays a graphic associated with diabetes 908 on the picture of the human body 910 based on the individual's elevated risks of developing that condition. However, the disease risk location identification interface 906 does not display a graphic associated with colon cancer because the individual's risk of developing colon cancer is not above the display threshold for colon cancer.

Figure 10:
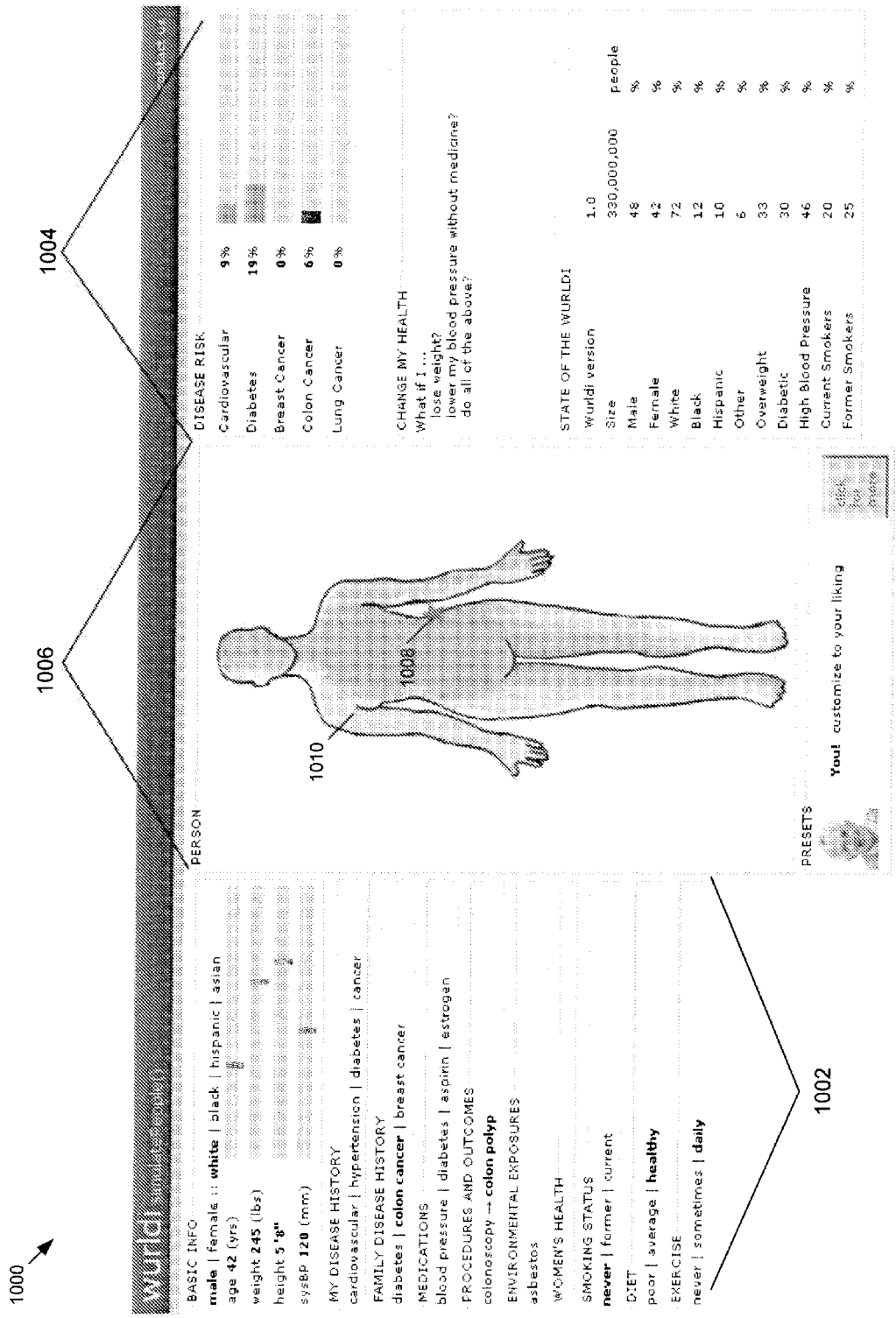
FIG. 10 depicts a graphical user interface having certain values entered into the health parameter entry interface, including a family history of colon cancer and a personal colonoscopy that revealed a colon polyp.

FIG. 10 depicts a graphical user interface 1000 having certain values entered into the health parameter entry interface 1002, including a family history of colon cancer and a personal colonoscopy that revealed a colon polyp. In the example of FIG. 10, the individual is noted as being a white male, aged 42, 5 feet, 8 inches tall, weighting 245 pounds, having a systolic blood pressure of 120. The individual is further noted as having a family history of colon cancer and as having had a colonoscopy performed that discovered a colon polyp. The individual has never smoked, has a healthy diet, and exercises regularly.

The disease risk interface 1004 depicts an alphanumeric representation of the risks of the individual developing certain health conditions based on the values entered in the health parameter entry interface 1002. Because the individual is noted as having a family history of colon cancer and as having had a colonoscopy that discovered a colon polyp, the individual's colon cancer risk is tripled to 6% over the individual depicted in FIG. 7 having similar values for several health parameters. The disease risk location identification interface 1006 displays a graphic associated with diabetes 1008 on the picture of the human body 1010 based on the individual's elevated risks of developing that condition. However, the disease risk location identification interface 1006 does not display a graphic associated with colon cancer because the individual's risk of developing colon cancer is not above the display threshold for colon cancer.

Figure 11:
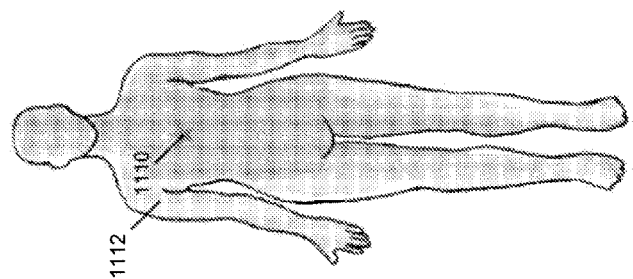
FIG. 11 depicts a graphical user interface having certain values entered into the health parameter entry interface for a woman.

FIG. 11 depicts a graphical user interface 1100 having certain values entered into the health parameter entry interface 1102 for a woman. In the example of FIG. 11, the individual is noted as being a white female, aged 32, 5 feet, 5 inches tall, weighting 131 pounds, and having a systolic blood pressure of 120. The individual has never smoked, has a healthy diet, and exercises regularly. Because the individual is noted as being a female, the women's health field 1104 of the health parameter entry interface 1102 is activated. The women's health field 1104 includes controls for entering data regarding whether an individual had a breast biopsy, when the individual had a first period, and when an individual first gave birth.

The disease risk interface 1106 includes an alphanumeric depiction or risks of the individual developing one or more health conditions based on the values entered in the health parameter entry interface 1104. In the example of FIG. 11, the individual has a 2% risk for developing cardiovascular disease, an 8% risk for developing diabetes, a 37% risk for developing breast cancer, a 6% risk for developing colon cancer, and a 0% risk of developing lung cancer. The disease risk location identification interface 1108 displays a graphic associated with breast cancer 1110 on the picture of the human body 1112 based on the individual's elevated risks of developing that condition.

Figure 12:
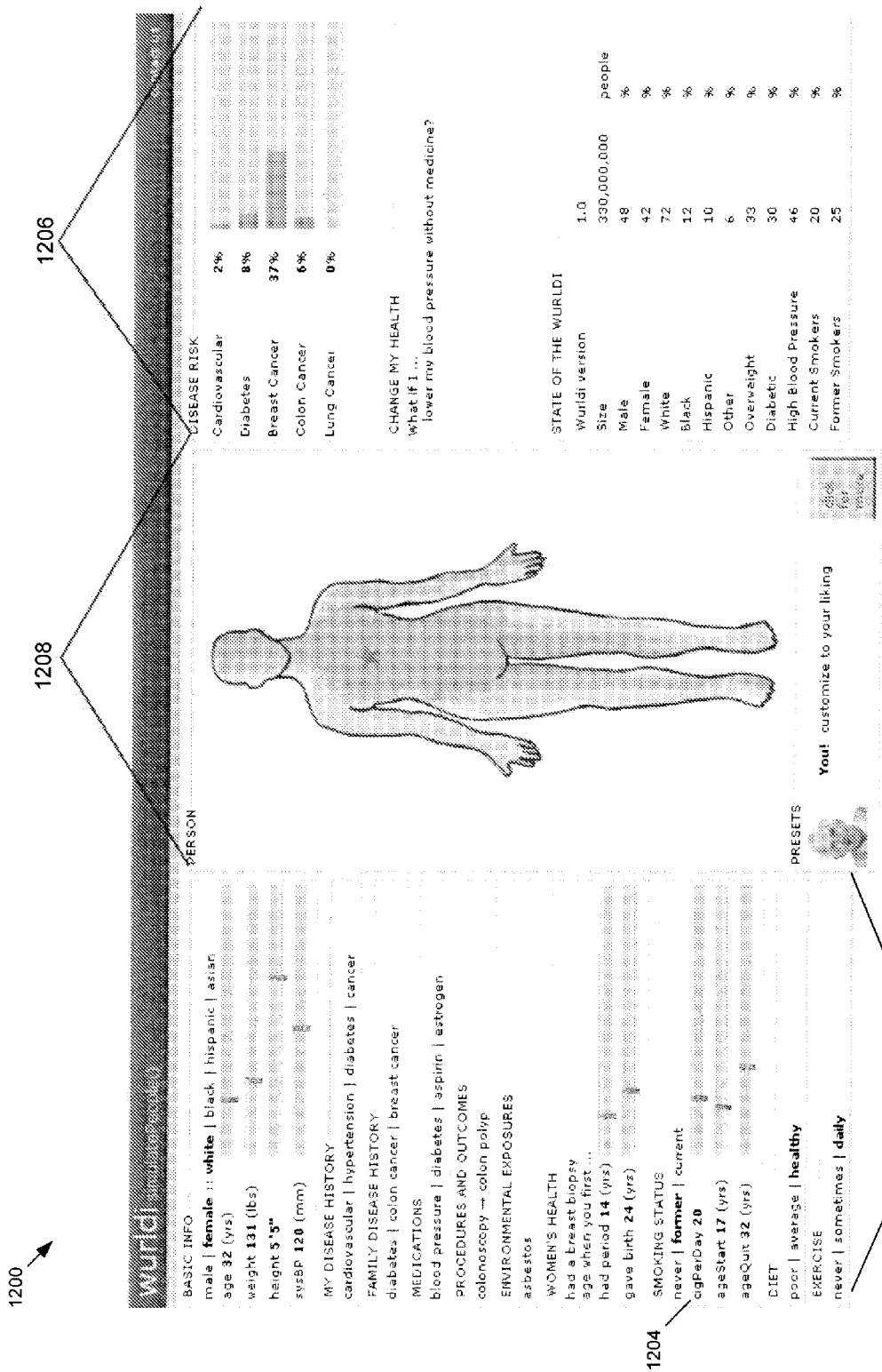
FIG. 12 depicts a graphical user interface having certain values entered into the health parameter entry interface including a smoking history.

FIG. 12 depicts a graphical user interface 1200 having certain values entered into the health parameter entry interface 1202 including a smoking history. In the example of FIG. 12, the individual is noted as being a white female, aged 32, 5 feet, 5 inches tall, weighting 131 pounds, and having a systolic blood pressure of 120. The individual has a healthy diet and exercises regularly, and is noted as a smoker. Because the individual is noted as being a smoker, the smoking status field 1204 of the health parameter entry interface 1202 is activated. The smoking status field 1204 includes controls for entering data regarding how many cigarettes the individual averaged while a smoker, the age the individual started smoking, and the age the individual quit smoking. In the example of FIG. 12, the individual is noted as smoking 20 cigarettes per day from the age of 17 to the age of 32. These values are considered by the real-time health risk assessment generator in calculating risks for certain diseases, which are displayed in the disease risk interface 1206 as well as the disease risk location identification interface 1208.

Figure 13:
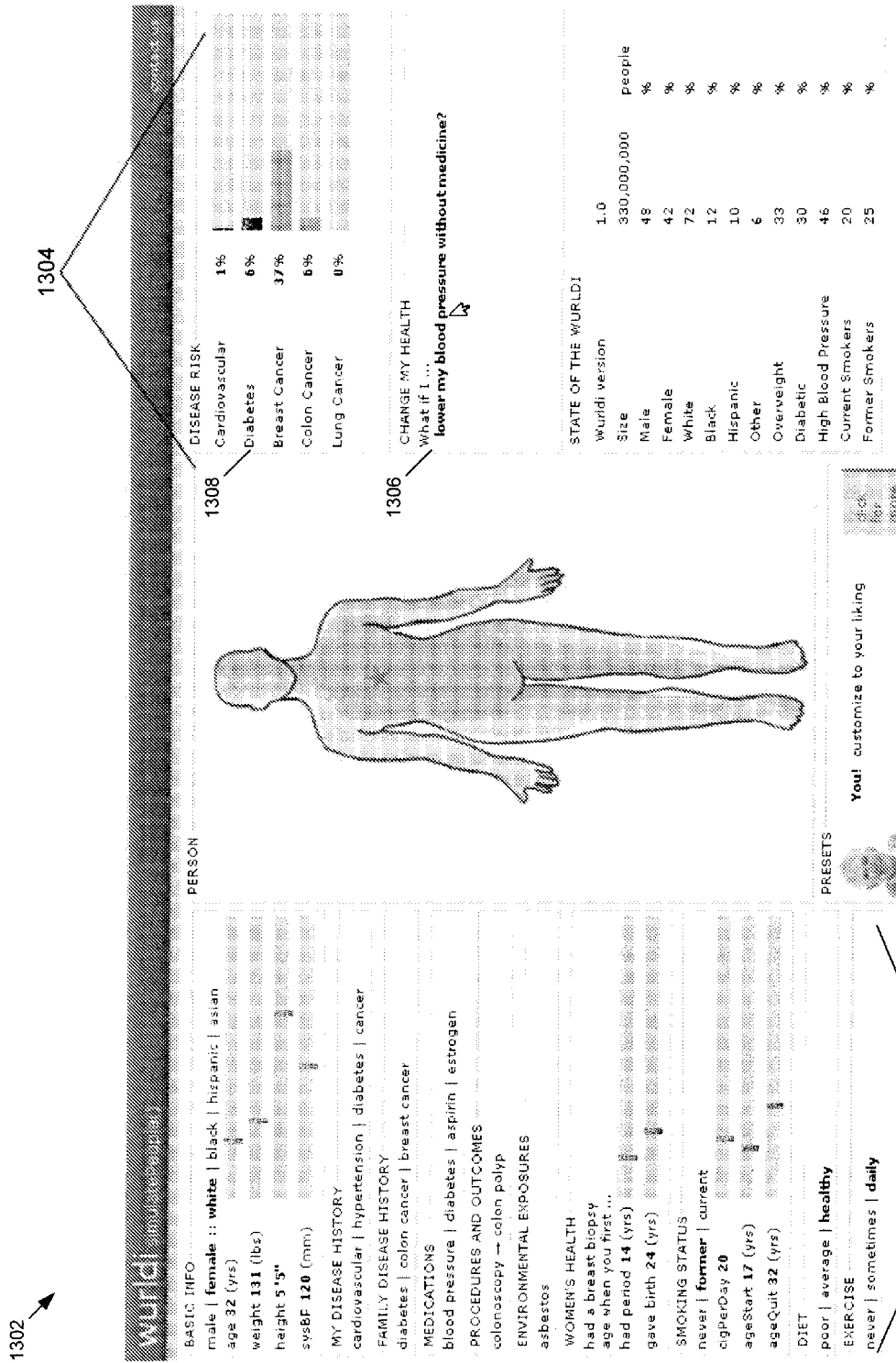
FIG. 13 depicts a graphical user interface having certain values entered into the health parameter entry interface, wherein a health improvement behavior is included in the disease risk interface.

FIG. 13 depicts a graphical user interface 1300 having certain values entered into the health parameter entry interface 1302, wherein a health improvement behavior 1306 is included in the disease risk interface 1304. In the example of FIG. 13, the individual is noted as being a white female, aged 32, 5 feet, 5 inches tall, weighting 131 pounds, and having a systolic blood pressure of 120. The individual has a healthy diet and exercises regularly, and is noted as a smoker. Based on the values entered into the health parameter entry interface, the disease risk interface 1304 displays an alphanumeric depiction of risks of a person developing one or more health conditions.

The disease risk interface 1304 further provides a health improvement behavior 1306, which the user has selected. The health improvement behavior 1306 asks what would happen to the risks of the individual developing the one or more health conditions if the individual adopted the behavior. When the user selects the behavior, such as by performing a mouse over operation or a clicking operation, the risks of the individual developing the one or more health conditions displayed at 1308 are updated to show the changed risk based on adoption of the selected behavior 1306. In the example of FIG. 13, the individual's risk for cardiovascular disease decreases by 1% over the example of FIG. 12, and the individual's risk for diabetes decreases by 2% over the example of FIG. 12 when the individual adopts the displayed health improvement behavior 1306. The updated risk levels for the one or more health conditions may be calculated in a variety of ways. For example, the formulas described above with respect to FIG. 6 may be modified to include a term related to the displayed health improvement behavior.

Figure 14:
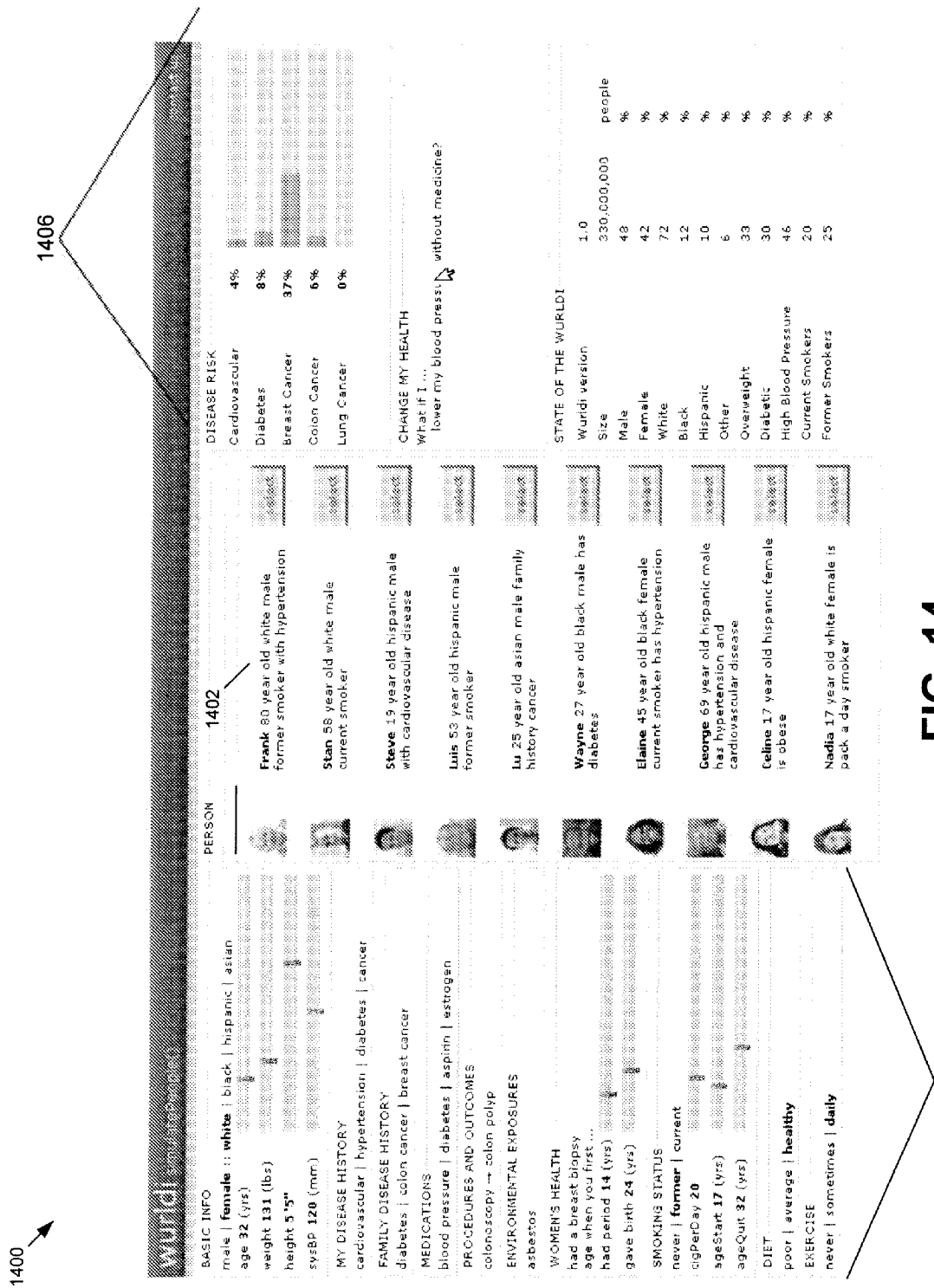
FIG. 14 depicts a graphical user interface that includes a plurality of templates and/or saved profiles for selection.

FIG. 14 depicts a graphical user interface 1400 that includes a plurality of templates and/or saved profiles 1402 for selection. Upon selection of one of the displayed records 1402, a set of values for the plurality of health parameters displayed in the health parameter entry interface 1404 may be loaded, with the health parameter entry interface 1404 and the disease risk interface 1406 being updated accordingly. The displayed records 1402 may be a set of templates for a user to use to help "jump-start" value entry for an individual. For example, the user may select a record 1402 that is similar to the individual that the user wishes to evaluate. The user can then customize the loaded values to better match the individual. In another embodiment, the records may represent saved records for individuals. For example, a user may activate a control to save values for the health parameters for a user after entering them for later access. The user may enter a short description of the individual, or such a description may be automatically generated based on the health parameter values being saved.

Figure 15:
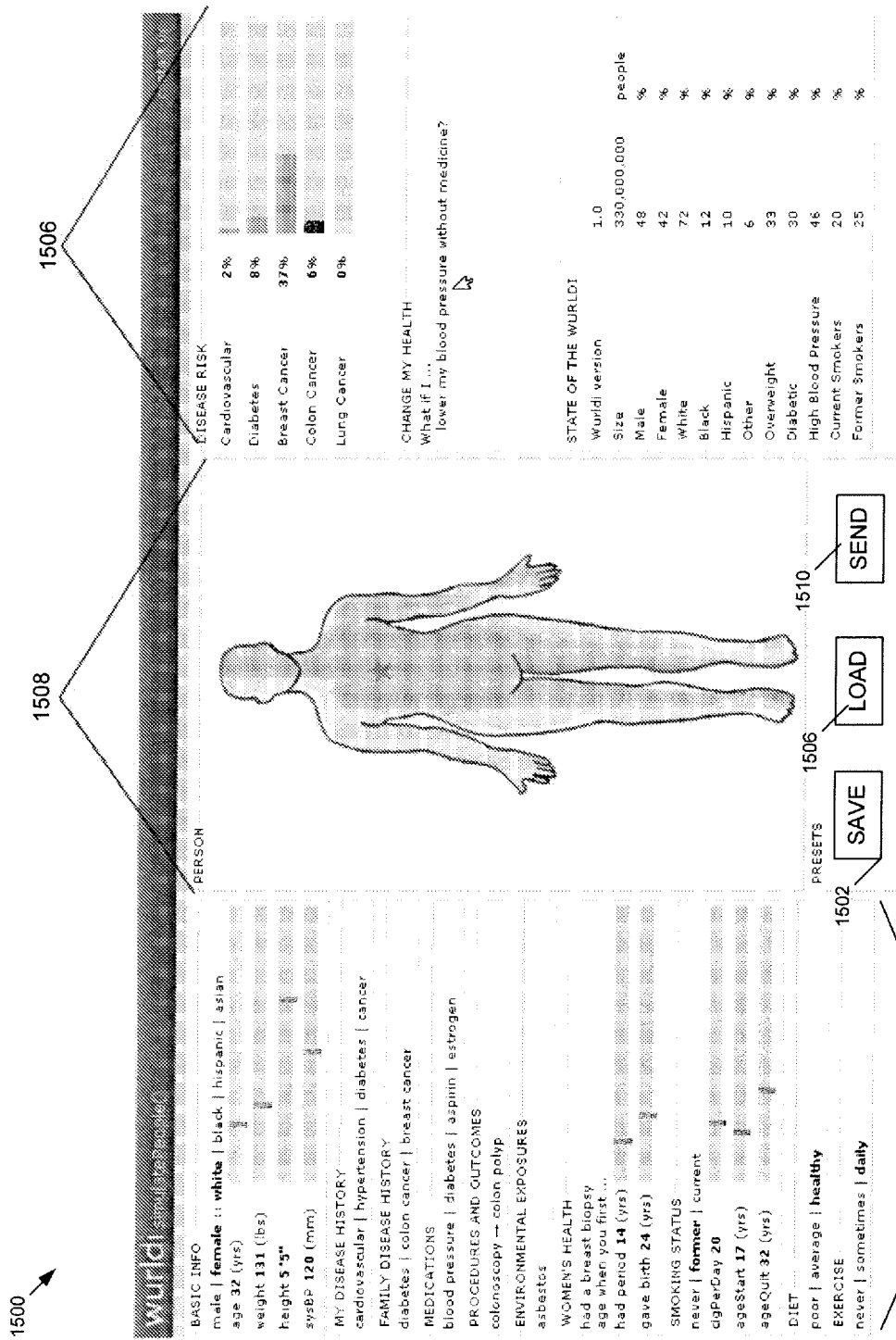
FIG. 15 depicts a graphical user interface that includes example controls for saving, loading, and sending values for health parameters.

FIG. 15 depicts a graphical user interface 1500 that includes example controls for saving, loading, and sending values for health parameters. A first control 1502 enables a user to save values for health parameters entered into the health parameter entry interface 1504. Upon selecting the save control 1502, the current values of the health parameters may be stored in persistent memory along with a description of the individual with which those values are associated. Such a description may include a name, patient number, customer number, a user entered description, or other data. The saved health parameter values may be stored for subsequent access by the real-time health risk assessment generator or for use by another application.

The graphical user interface further includes a second control 1506 for loading values for health parameters. Selection of the load control 1506 may access a selection display such as the display shown in FIG. 14 at 1402. Upon selection of a set of values for health parameters, those values may be loaded, shown in the health parameter entry interface 1504, and the disease risk interface 1506 and disease risk location identification interface 1508 may be updated accordingly.

The graphical user interface further includes a third control 1510 for sending values of health parameters. Upon selection of the send control 1510, the user may be prompted for a destination. The destination may be an e-mail address, where the values of the health parameters are sent via e-mail as a body of a message or an attachment. The destination may further be an address, where the values of the health parameters are sent to the address as a file or a data record for storage. The destination may also be a service. For example, values of the health parameters may be sent to a third party, such as Google Health.

Figure 16:
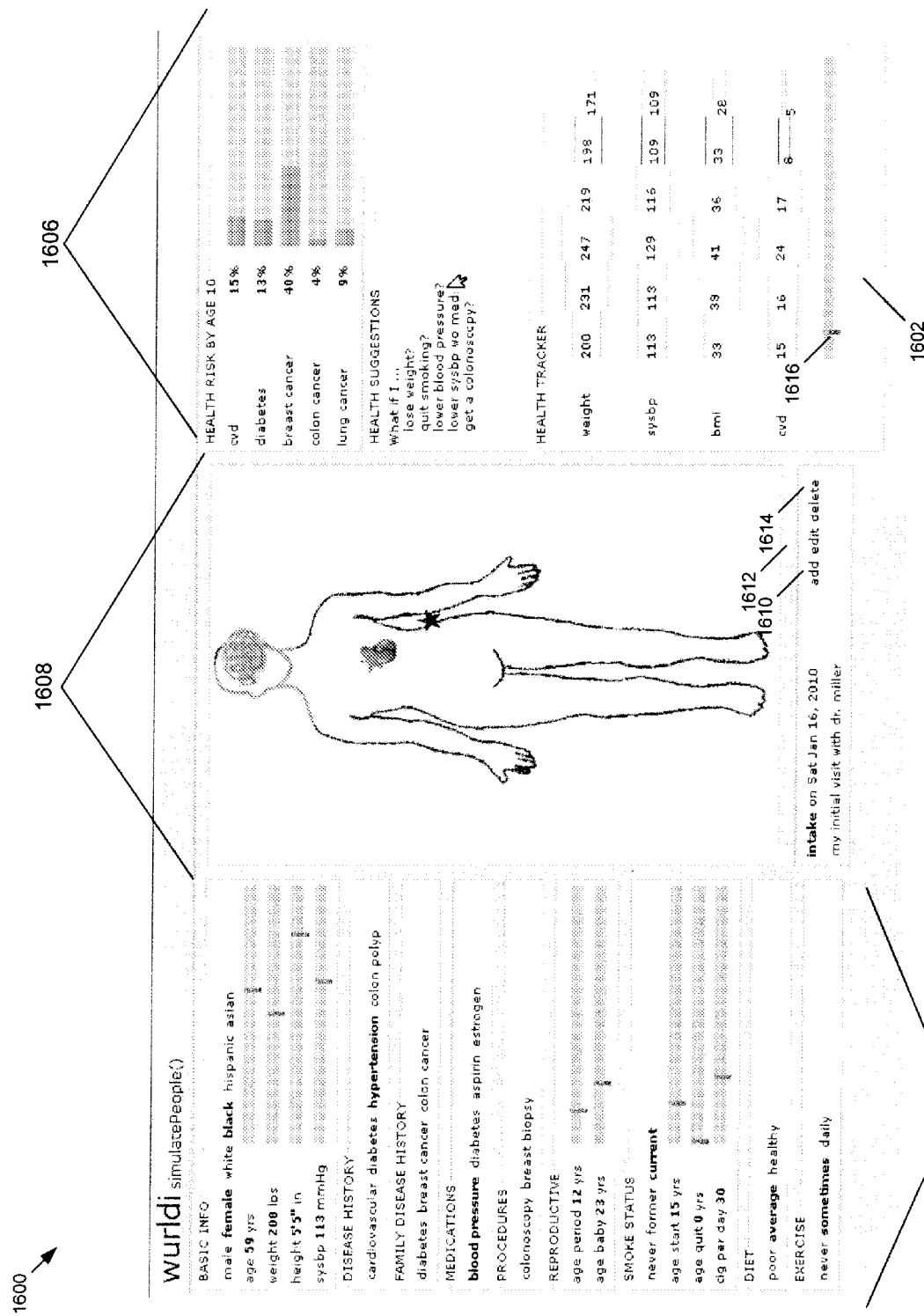
FIG. 16 displays a graphical user interface that includes a health parameter value history.

FIG. 16 displays a graphical user interface 1600 that includes a health history interface 1602. The graphical user interface 1600 includes a health parameter entry interface 1604 that displays values related to a plurality of health parameters. The graphical user interface 1600 further includes a disease risk interface 1606 that displays risks of an individual developing one or more health conditions based on the values of the health parameter entry interface 1604, and the graphical user interface 1600 further includes a disease risk location identification interface 1608 that displays graphics on a depiction of a human body based on the risk levels shown in the disease risk interface 1606.

The graphical user interface 1600 also includes a health history interface 1602. The health history interface 1602 displays, both numerically and graphically, values for a plurality of the health parameters at different points and time. For example, a user may enter values for the health parameters for an individual into the health parameter entry interface 1604. When the user is satisfied with the entered values, the user may click an add control 1610 to add the values entered into the health parameter entry interface 1604 to the health history interface 1602. The user may be prompted to input a title, description, and/or date for the current values. The values are saved and displayed on the health history interface 1602. Sets of health parameter values can also be edited or deleted using controls 1612, 1614, respectively.

The columns in the health history interface 1602 may be sorted from left to right according to date, where the set of values associated with the earliest date is displayed in a leftmost column. A slider 1616 enables selection of different ones of the sets of health parameter values. The example of FIG. 16 depicts selection of the first column, where the individual has a weight of 200, a systolic blood pressure of 113, a body mass index of 33, and a cardiovascular score of 15. When the slider 1616 is moved, the values of the health parameter entry interface 1604, the risks in the disease risk interface 1606, and the graphics in the disease risk location identification interface 1608 are updated accordingly. The numeric values in the health history interface 1602 may be displayed along with a graphical identifier, such as parallel bars shaded in between where the height of the parallel bars represents the magnitude of the numeric value. Using such a graphical identifier, a user can easily compare the numeric values for a row across the periods of time represented in the health history interface 1602.

Figure 17:
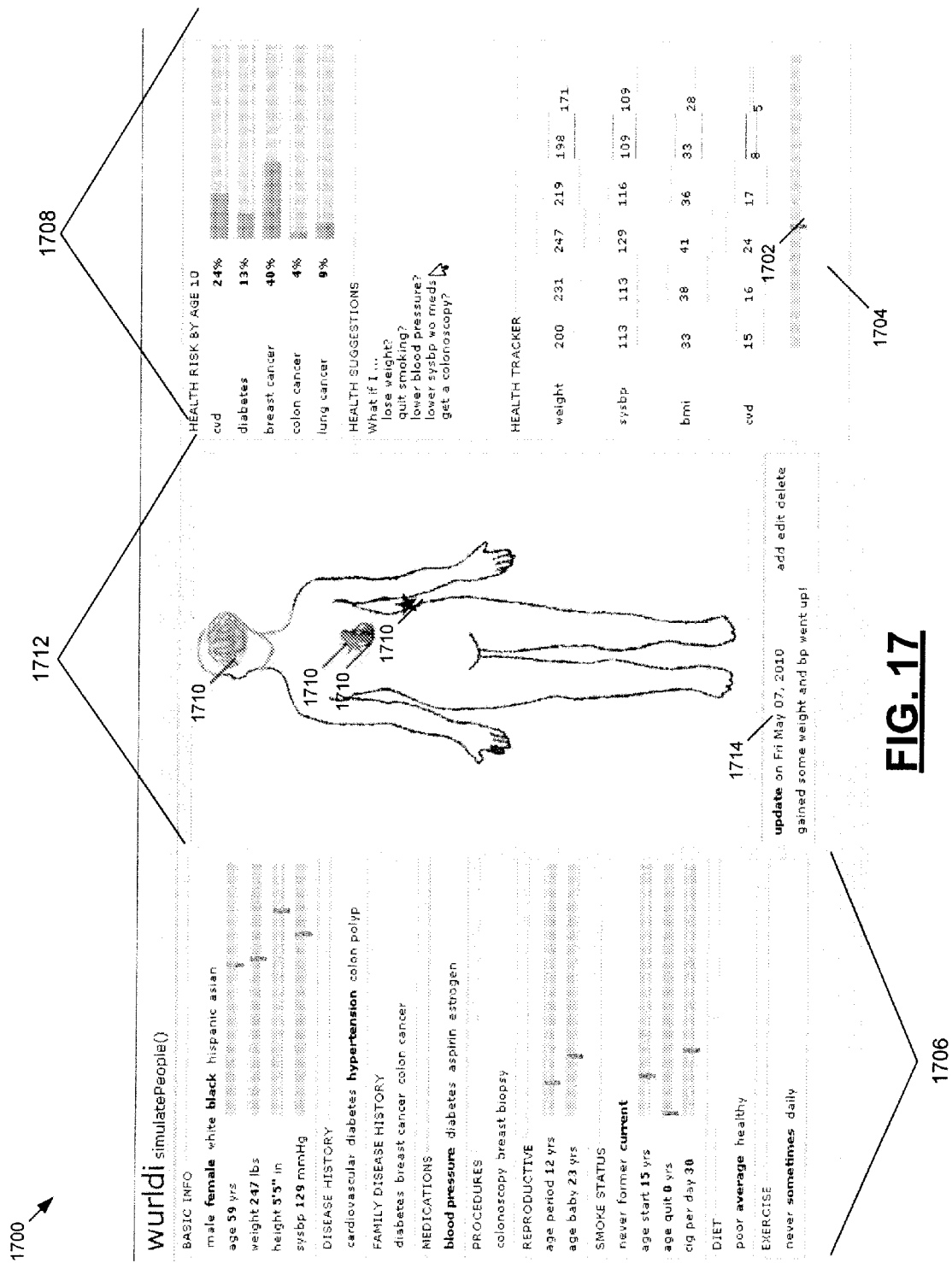
FIG. 17 depicts a graphical user interface, where a slider in a health history interface has been moved to a second position.

FIG. 17 depicts a graphical user interface 1700, where a slider 1702 in a health history interface 1704 has been moved to a second position. Upon moving the slider 1702 to the second position, the values in the health parameter entry interface 1706, the risks in the disease risk interface 1708 and the graphics 1710 in the disease risk location identification interface 1712 are updated accordingly. A title, description, and date associated with the slider position are also displayed at 1714.

Figure 18:
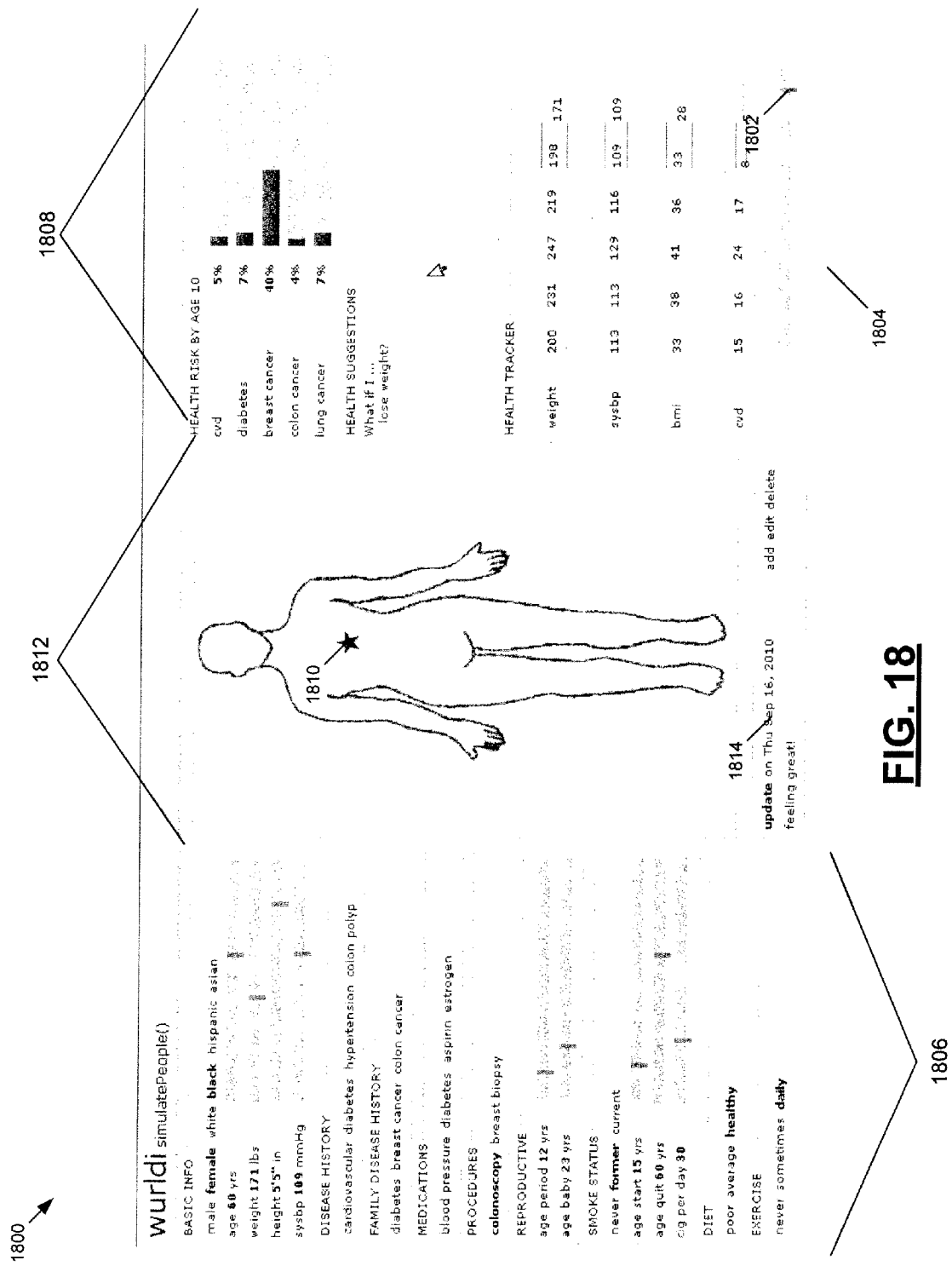
FIG. 18 depicts a graphical user interface, where a slider in a health history interface has been moved to a third position.

FIG. 18 depicts a graphical user interface 1800, where a slider 1802 in a health history interface 1804 has been moved to a third position. Upon moving the slider 1802 to the third position, the values in the health parameter entry interface 1806, the risks in the disease risk interface 188 and the graphics 1810 in the disease risk location identification interface 1812 are updated accordingly. A title, description, and date associated with the slider position are also displayed at 1814.

This specification includes a number of examples of implementations of a real-time health assessment generator. Additional examples are contemplated as well. For example, a picture of a human body displayed in a disease risk location identification interface may be modified according to values for health parameters entered in the health parameter entry interface. For example, the picture of the human body may be modified based on sex, race, age, weight, height or other parameter values entered. The picture of the human body may be further user customizable (e.g., via a head-shot picture) to further represent an individual being assessed. A real-time health assessment generator can be implemented in a variety of manners including via an Ajax programming language.

Figure 19A:
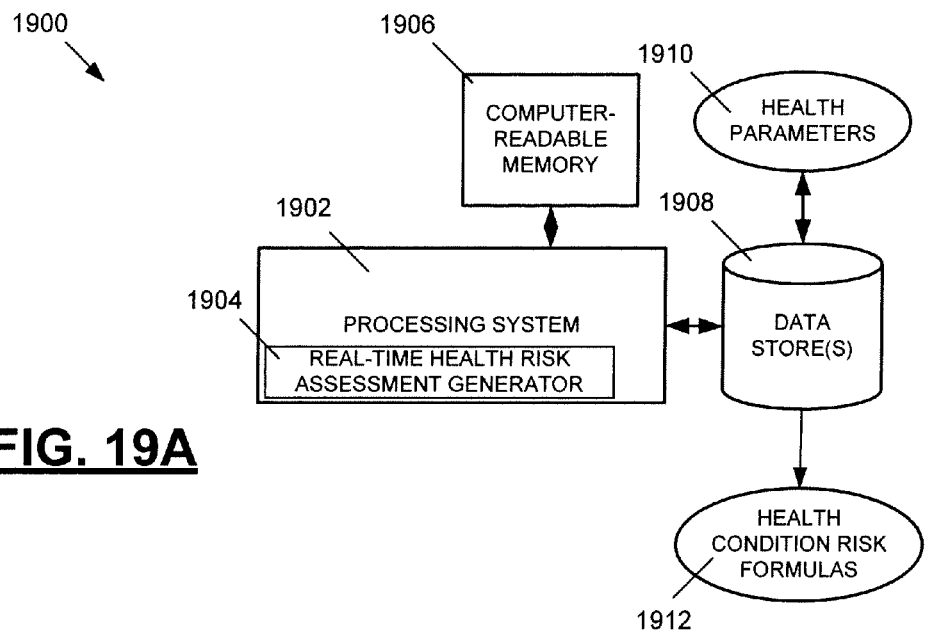
FIGS. 19A, 19B, and 19C depict example systems of a real-time health risk assessment generator.
Figure 19B:
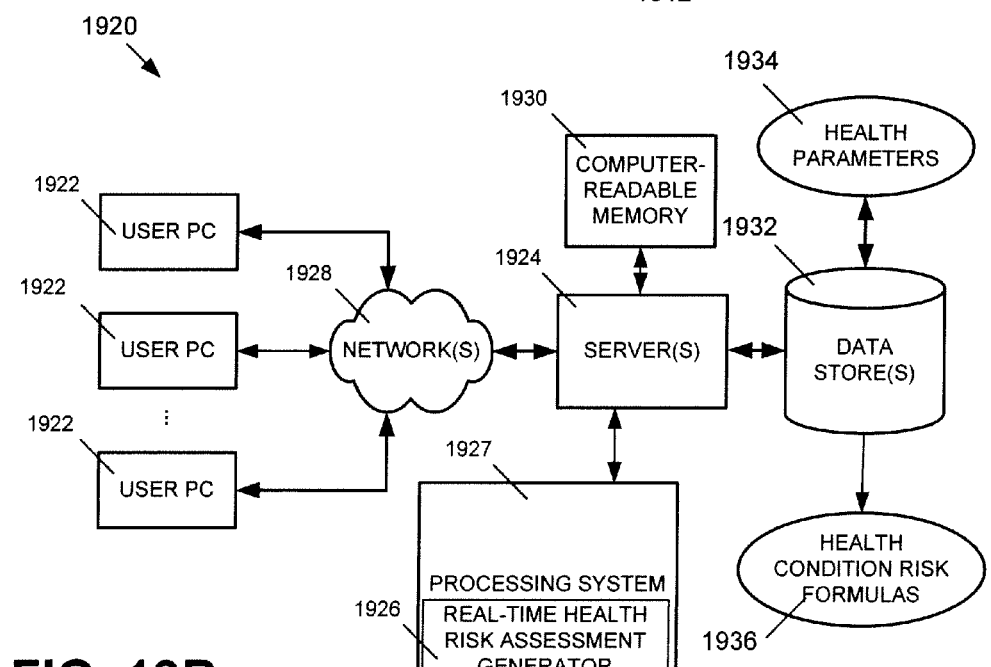
Figure 19C:
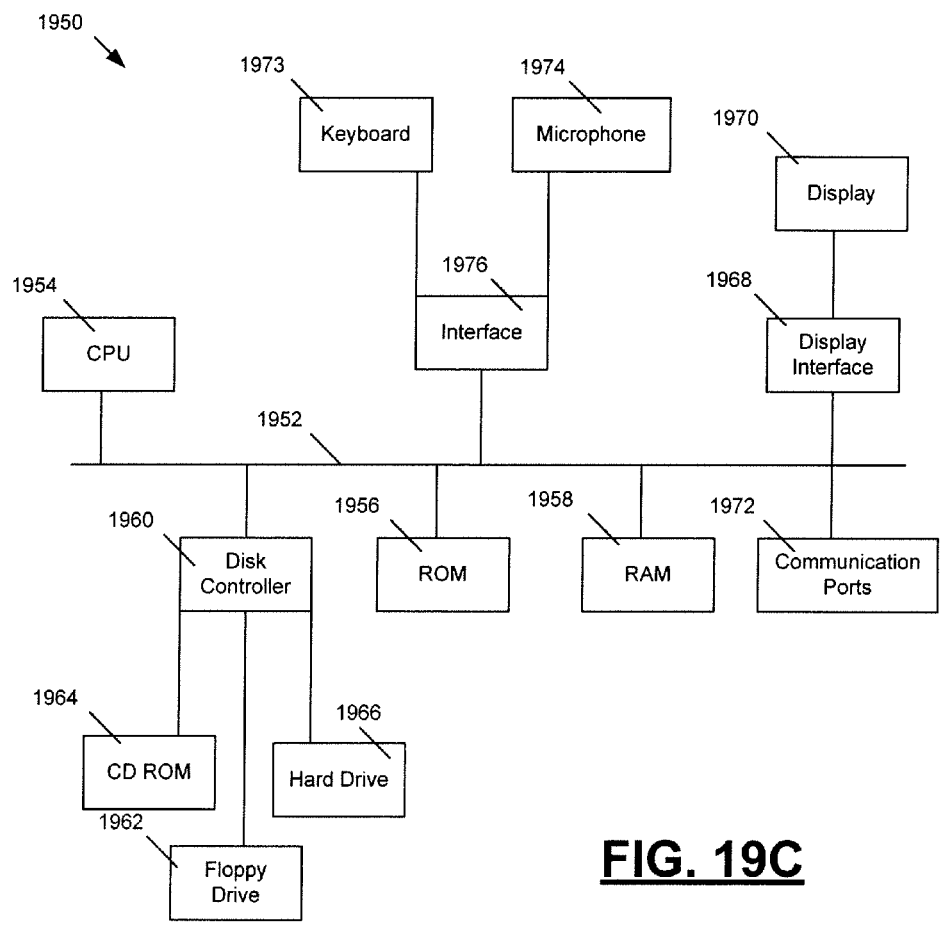

FIGS. 19A, 19B, and 19C depict example systems for a real-time health risk assessment generator. For example, FIG. 19A depicts an exemplary system 1900 that includes a stand alone computer architecture where a processing system 1902 (e.g., one or more computer processors) includes a real-time health risk assessment generator 1904 being executed on it. The processing system 1902 has access to a computer-readable memory 1906 in addition to one or more data stores 1908. The one or more data stores 1908 may contain health parameter values 1910 as well health condition risk formulas 1912.

FIG. 19B depicts a system 1920 that includes a client server architecture. One or more user PCs 1922 accesses one or more servers 1924 running a real-time health risk assessment generator 1926 on a processing system 1927 via one or more networks 1928. The one or more servers 1924 may access a computer readable memory 1930 as well as one or more data stores 1932. The one or more data stores 1932 may contain health parameter values 1934 as well as health condition risk formulas 1936.

FIG. 19C shows a block diagram of exemplary hardware for a stand alone computer architecture 1950, such as the architecture depicted in FIG. 19A, that may be used to contain and/or implement the program instructions of system embodiments described herein. A bus 1952 may serve as the information highway interconnecting the other illustrated components of the hardware. A processing system 1954 labeled CPU (central processing unit) (e.g., one or more computer processors), may perform calculations and logic operations required to execute a program. A processor-readable storage medium, such as read only memory (ROM) 1956 and random access memory (RAM) 1958, may be in communication with the processing system 1954 and may contain one or more programming instructions for a real-time health risk assessment generator. Optionally, program instructions may be stored on a computer readable storage medium such as a magnetic disk, optical disk, recordable memory device, flash memory, or other physical storage medium. Computer instructions may also be communicated via a communications signal, or a modulated carrier wave.

A disk controller 1960 interfaces with one or more optional disk drives to the system bus 1952. These disk drives may be external or internal floppy disk drives such as 1962, external or internal CD-ROM, CD-R, CD-RW or DVD drives such as 1964, or external or internal hard drives 1966. As indicated previously, these various disk drives and disk controllers are optional devices.

Each of the element managers, real-time data buffer, conveyors, file input processor, database index shared access memory loader, reference data buffer and data managers may include a software application stored in one or more of the disk drives connected to the disk controller 1960, the ROM 1956 and/or the RAM 1958. Preferably, the processor 1954 may access each component as required.

A display interface 1968 may permit information from the bus 1952 to be displayed on a display 1970 in audio, graphic, or alphanumeric format. Communication with external devices may optionally occur using various communication ports 1972.

In addition to the standard computer-type components, the hardware may also include data input devices, such as a keyboard 1973, or other input device 1974, such as a microphone, remote control, pointer, mouse and/or joystick.

Embodiments of the subject matter and the functional operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer program products, i.e., one or more modules of computer program instructions encoded on a computer-readable medium for execution by, or to control the operation of, data processing apparatus.

The computer-readable medium can be a machine-readable storage device, a machine-readable storage substrate, a memory device, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal, that is generated to encode information for transmission to suitable receiver apparatus.

While this specification contains many specifics, these should not be construed as limitations on the scope of the invention or of what may be claimed, but rather as descriptions of features specific to particular embodiments of the invention. Certain features that are described in this specification in the context or separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the invention have been described. Other embodiments are within the scope of the following claims. For example, the actions recited in the claims can be performed in a different order and still achieve desirable results It is claimed:

1. A non-transitory computer readable storage medium storing one or more programs, the one or more programs comprising instructions, which, when executed by an electronic device with one or more processors, cause the electronic device to perform operations comprising:

displaying a health parameter entry interface on a first portion of a computer display, the health parameter entry interface including a plurality of health parameter controls for manipulation to enter values for a corresponding plurality of health parameters, wherein a first health parameter in the plurality of health parameters corresponds to a first health parameter control in the plurality of health parameter controls and wherein the first health parameter control is a sliding bar control, wherein a displayed (x,y) position of the sliding bar control on the computer display determines a corresponding value for the first health parameter;

displaying a disease risk interface on a second portion of the computer display, the disease risk interface including an alphanumeric depiction of risks of a person developing one or more health conditions based on the values entered for the plurality of health parameters using the health parameter entry interface;

displaying a disease risk location identification interface on a third portion of the computer display, wherein the first portion, the second portion, and the third portion of the display are each different nonoverlapping portions of the display, the disease risk location identification interface including a picture of all or a portion of a human body, wherein the health parameter entry interface, the disease risk interface, and the disease risk location identification interface are concurrently displayed on the computer display;

detecting a change in the displayed (x,y) position of the sliding bar control;

updating a value of the first health parameter in accordance with the change in the displayed (x,y) position of the sliding bar control;

updating an alphanumeric depiction of a risk of a person developing a first health condition in the one or more health conditions in the disease risk interface based, at least in part, on the updated value of the first health parameter;

displaying a graphic on the picture of said all or said portion of the human body at a position of the human body associated with the first health condition when the updated alphanumeric depiction of a risk of a person developing the first health condition satisfies a display threshold;

not displaying the graphic on the picture of said all or said portion of the human body at a position of the human body associated with the first health condition when the updated alphanumeric depiction of a risk of a person developing the first health condition does not satisfy the display threshold, thereby causing the alphanumeric depiction of risks of a person developing one or more health conditions and the display of graphics on the picture of said all or said portion of the human body to be updated substantially concurrently to changes to the plurality of health parameters in the health parameter entry interface.

2. The non-transitory computer readable storage medium of claim 1, the one or more programs further comprising instructions for detecting an adjustment of the first health parameter using the sliding bar control via a mouse click-drag-release operation or mouse click-drag operation, wherein the alphanumeric depiction of the risk of a person developing the first health conditions and the display of the graphic on the picture of the human body are updated upon the mouse release or the mouse drag.

3. The non-transitory computer readable storage medium of claim 1, wherein the plurality of health parameters includes sex, race, age, weight, and height of a person.

4. The non-transitory computer readable storage medium of claim 3, wherein the plurality of health parameters further includes blood pressure.

5. The non-transitory computer readable storage medium of claim 1, wherein the plurality of health parameters includes an identification of a history of cardiovascular disease, an identification of a history of hypertension, an identification of a history of diabetes, and an identification of a history of cancer.

6. The non-transitory computer readable storage medium of claim 1, the one or more programs further comprising instructions for selecting a health parameter in the plurality of health parameters by detecting a mouse click on a name of a disease without use of any other selection control.

7. The non-transitory computer readable storage medium of claim 1, wherein the plurality of health parameters comprises a plurality of family history parameters that includes parameters identifying a history of diabetes, colon cancer, and breast cancer.

8. The non-transitory computer readable storage medium of claim 1, wherein the health parameter interface displays at least one parameter from the group of parameters comprising:
   a medication parameter;
   a received procedures parameter;
   an environmental exposure parameter;
   a women's health parameter;
   a smoking parameter;
   a diet parameter; and
   an exercise parameter.

9. The non-transitory computer readable storage medium of claim 1, wherein the plurality of health parameters includes a smoking status parameter, a smoking start age parameter, and a smoking quit age parameter.

10. The non-transitory computer readable storage medium of claim 1, wherein the disease risk interface includes an alphanumeric depiction of a risk of a person developing:
    cardiovascular disease;
    diabetes;
    breast cancer;
    colon cancer; and
    lung cancer.

11. The non-transitory computer readable storage medium of claim 1, wherein
    the disease risk interface further includes an indication of a health improvement behavior,
    the health improvement behavior provided is based on values of the risks of a person developing the one or more health conditions.

12. The non-transitory computer readable storage medium of claim 11, wherein the health improvement behavior is related to lowering cardiovascular disease risk that is displayed when a risk for cardiovascular disease for a person is greater than a behavior display threshold.

13. The non-transitory computer readable storage medium of claim 11, the one or more programs further comprising instructions for the listing of risks of a person developing the one or more health conditions to account for a person performing an action associated with the health improvement behavior.

14. The non-transitory computer readable storage medium of claim 1, wherein the picture of said all or said portion of the human body is generated based on the plurality of health parameters.

15. The non-transitory computer readable storage medium of claim 14, wherein the picture of said all or said portion of the human body is generated based on one of the group of health parameters consisting of:
sex;
race;
age;
weight; and
height.

16. The non-transitory computer readable storage medium of claim 1, wherein a user entering the plurality of health parameters is not the person with which the plurality of health parameters are associated.

17. The non-transitory computer readable storage medium of claim 1, the one or more programs further comprising providing a save/load profile interface.

18. The non-transitory computer readable storage medium of claim 1, the one or more programs further comprising instructions for providing an insurance quote based on the risks of a person developing the one or more health conditions.

19. The non-transitory computer readable storage medium of claim 1, the one or more programs further comprising instructions for providing a formula display, wherein the formula display shows a formula used to calculate a risk of a person developing a health condition.

20. The non-transitory computer readable storage medium of claim 1, wherein
the health parameter entry interface is displayed on approximately a first columnar third of the computer display,
the disease risk location identification interface is displayed on approximately a second columnar third of the computer display, and
the disease risk interface is displayed on approximately a third columnar third of the computer display.

21. The non-transitory computer readable storage medium of claim 1, the one or more programs further comprising instructions for providing the computer display via a webpage.

22. The non-transitory computer readable storage medium of claim 1, the one or more programs further comprising instructions for updating substantially simultaneously the listing of risks of a person developing the one or more health conditions and the display of graphics on the picture of said all or said portion of the human body with changes to the plurality of health parameters in the health parameter entry interface without utilization of a submit button or other submit control.

23. The non-transitory computer readable storage medium of claim 1, the one or more programs further comprising instructions for providing a health history interface, wherein
the health history interface displays the values for more than one of the plurality of health parameters at different points in time,
the health history interface includes a selection control for selecting one of the different points in time, and
the health parameter entry interface, the disease risk interface, and the disease risk location interface are updated when the selection control is manipulated.

24. The non-transitory computer readable storage medium of claim 23, wherein the selection control is a slide bar and wherein the health history interface displays the values graphically and numerically.

25. The non-transitory computer readable storage medium of claim 1, wherein the computer display is provided via a smart phone application.

* * * * *